United States Patent [19]
Akahane et al.

[11] Patent Number: 6,124,456
[45] Date of Patent: Sep. 26, 2000

[54] PYRAZOLOPYRIDINE COMPOUND AND PHARMACEUTICAL USE THEREOF

[75] Inventors: Atsushi Akahane, Hyogo; Satoru Kuroda, Takatsuki; Hiromichi Itani, Hyogo; Yasuyo Shimizu, Osaka, all of Japan

[73] Assignee: Fujisawa Pharmaceutical Co., Ltd., Osaka, Japan

[21] Appl. No.: 09/147,543

[22] PCT Filed: Jul. 17, 1997

[86] PCT No.: PCT/JP97/02493

§ 371 Date: Jan. 19, 1999

§ 102(e) Date: Jan. 19, 1999

[87] PCT Pub. No.: WO98/03507

PCT Pub. Date: Jan. 29, 1998

[30] Foreign Application Priority Data

Jul. 18, 1996 [AU] Australia ............................. PO 1110

[51] Int. Cl.[7] ....................... C07D 471/04; A61K 31/497
[52] U.S. Cl. ...................... 544/252.02; 544/238
[58] Field of Search ........................ 544/238; 514/252.02

[56] References Cited

U.S. PATENT DOCUMENTS

| | | |
|---|---|---|
| 4,925,849 | 5/1990 | Shiokawa et al. . |
| 4,994,453 | 2/1991 | Shiokawa et al. . |
| 5,087,629 | 2/1992 | Shiokawa et al. . |
| 5,102,869 | 4/1992 | Shiokawa et al. . |
| 5,102,878 | 4/1992 | Shiokawa et al. . |
| 5,155,114 | 10/1992 | Shiokawa et al. . |
| 5,179,103 | 1/1993 | Shiokawa et al. . |
| 5,204,346 | 4/1993 | Shiokawa et al. . |
| 5,234,930 | 8/1993 | Shiokawa et al. . |
| 5,296,490 | 3/1994 | Shiokawa et al. . |
| 5,338,743 | 8/1994 | Shiokawa et al. . |
| 5,773,530 | 6/1998 | Akahane et al. . |

*Primary Examiner*—Robert Gerstl
*Attorney, Agent, or Firm*—Oblon, Spivak, McClelland, Maier & Neustadt, P.C.

[57] ABSTRACT

A pyrazolopyridine compound of formula (I) wherein $R^1$ is aryl, and $R^2$ is lower alkyl substituted with unsaturated 3 to 8-membered heteromonocyclic group containing 1 or 2 sulfur atom(s) and 1 to 3 nitrogen atom(s) which may have one or more substituent(s); a group of formula (1) wherein $R^3$ is hydrogen, lower alkyl, ar(lower)alkyl or acyl, $R^4$ is hydrogen or hydroxy, A is lower alkylene, m is an integer of 0 or 1, and n is an integer of 1 or 2; a group of formula (2) wherein $R^5$ and $R^6$ are each lower alkyl; or quinuclidinyl, or a salt the The pyrazolopyridine compound (I) and a salt thereof of the present invention are adenosine antagonists and are useful for the prevention and/or treatment of depression, dementia (e.g. Alzheimer's disease, cerebrovascular dementia, Parkinson's disease, etc.), anxiety, pain, cerebrovascular disease (e.g. stroke, etc.), heart failure, and the like.

14 Claims, No Drawings

PYRAZOLOPYRIDINE COMPOUND AND PHARMACEUTICAL USE THEREOF

This Application is a 371 of PCT/JP97/02493 filed Jul. 17, 1997.

FIELD OF THE INVENTION

The present invention relates to a novel pyrazolopyridine compound and a salt thereof which are useful as medicaments.

BACKGROUND ART

Some pyrazolopyridine compounds to be useful as psychostimulant, remedy for renal failure, or the like are known (e.g. EP-0299209, EP-0379979, etc.).

DISCLOSURE OF THE INVENTION

The present invention relates to a novel pyrazolopyridine compound and a salt thereof useful as medicaments; processes for the preparation of said pyrazolopyridine compound and a salt thereof; a pharmaceutical composition comprising, as an active ingredient, said pyrazolopyridine compound or a pharmaceutically acceptable salt thereof; a use of said pyrazolopyridine compound or a pharmaceutically acceptable salt thereof as a medicament; and a method for using said pyrazolopyridine compound or a pharmaceutically acceptable salt thereof for therapeutic purposes, which comprises administering said pyrazolopyridine compound or pharmaceutically acceptable salt thereof to a human being or an animal.

The pyrazolopyridine compound and a salt thereof are adenosine antagonists (especially, $A_1$ receptor antagonist) and possess various pharmacological actions such as cognitive enhancing action, analgesic action, locomotor action, antidepressant action, diuretic action, cardioprotective effect, cardiotonic action, vasodilating action (e.g. cerebral vasodilating action, etc.), the action of increasing the renal blood flow, renal protective effect, improvement action of renal function, enhancing action of lipolysis, inhibition action of anaphylactic bronchoconstriction, acceleration action of the insulin release, the action of increasing the production of erythropoietin, inhibiting action of platelet aggregation, or the like.

They are useful as cognitive enhancer, antidementia drug, psychostimulant, analgesic, cardioprotective agent, antidepressant, ameliorants of cerebral circulation, tranquilizer, drug for heart failure, cardiotonic agent, antihypertensive agent, drug for renal failure (renal insufficiency), drug for renal toxicity, renal protective agent, drug for improvement of renal function, diuretic, drug for edema, anti-obesity, antiasthmatic, bronchodilator, drug for apnea, drug for gout, drug for hyperuricemia, drug for sudden infant death syndrome (SIDS), ameliorants of immunosuppressive action of adenosine, antidiabetic agent, drug for ulcer, drug for pancreatitis, drug for Meniere's syndrome, drug for anemia; drug for thrombosis, drug for myocardial infarction, drug for obstruction, drug for arteriosclerosis obliterans, drug for thrombophlebitis, drug for cerebral infarction, drug for transient ischemic attack, drug for angina pectoris, or the like; and useful for the prevention and/or treatment of depression, dementia (e.g. Alzheimer's disease, cerebrovascular dementia, Parkinson's disease, etc.), anxiety, pain, cerebrovascular disease (e.g. stroke, etc.), heart failure; hypertension (e.g. essential hypertension, nephrogenous hypertension, etc.); circulatory insufficiency (acute circulatory insufficiency) caused by, for example, ischemia/reperfusion injury (e.g. myocardial ischemia/reperfusion injury, cerebral ischemia/reperfusion injury, peripheral ischemia/reperfusion injury, etc.), shock (e.g. endotoxin shock, hemorrhagic shock, etc.), surgical procedures or the like; post-resuscitation asystole; bradyarrhythmia; electromechanical dissociation; hemodynamic collapse; SIRS (systemic inflammatory response syndrome); multiple organ failure; renal failure (renal insufficiency) (e.g. acute renal failure, etc.), renal toxicity [e.g. renal toxicity induced by a drug such as cisplatins, gentamicin, FR-900506 (disclosed in EP-0184162), cyclosporin (e.g. cyclosporin A) or the like; glycerol, etc.], nephrosis, nephritis, edema (e.g. cardiac edema, nephrotic edema, hepatic edema, idiopathic edema, drug edema, acute angioneurotic edema, hereditary angioneurotic edema, carcinomatous ascites, gestational edema, etc.); obesity, bronchial asthma, gout, hyperuricemia, sudden infant death syndrome, immunosuppression, diabetes, ulcer such as peptic ulcer (e.g. gastric ulcer, duodenal ulcer, etc.), pancreatitis, Meniere's syndrome, anemia, dialysis-induced hypotension, constipation, ischemic bowel disease, ileus (e.g. mechanical ileus, adynamic ileus, etc.); myocardial infarction, thrombosis (e.g. arterial thrombosis, cerebral thrombosis, etc.), obstruction, arteriosclerosis obliterans, thrombophlebitis, cerebral infarction, transient ischemic attack, angina pectoris, or the like.

The novel pyrazolopyridine compound of the present invention can be shown by the following formula (I).

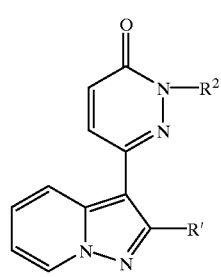

(I)

wherein $R^1$ is aryl, and $R^2$ is lower alkyl substituted with unsaturated 3 to 8-membered heteromonocyclic group containing 1 or 2 sulfur atom(s) and 1 to 3 nitrogen atom(s), which may have one or more substituent(s); a group of the formula:

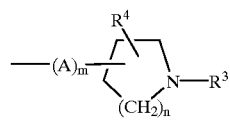

[wherein $R^3$ is hydrogen, lower alkyl, ar(lower)alkyl or acyl, $R^4$ is hydrogen or hydroxy, A is lower alkylene, m is an integer of 0 or 1, and n is an integer of 1 or 2];

a group of the formula:

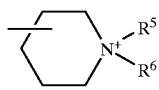
[wherein
R⁵ and R⁶ are each lower alkyl]; or quinuclidinyl, or a salt thereof.
The object compound (I) and a salt thereof of the present invention can be prepared by the following reaction schemes.
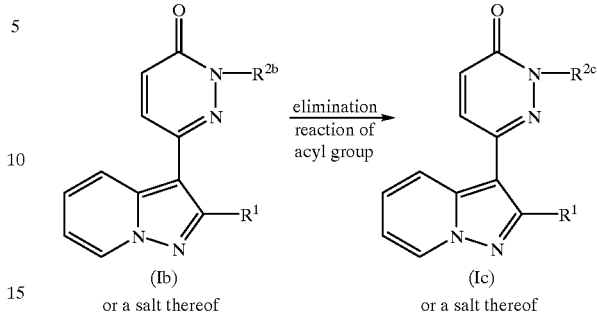

Process 6

(Ic) or a salt thereof acylation reaction →

(Ib) or a salt thereof

Process 7

(V) or a salt thereof formation reaction of thiazole ring →

(If) or a salt thereof wherein
R$^1$ and R$^2$ are each as defined above,
R$^{3a}$ is acyl,
R$^{2b}$ is a group of formula:

$$—(A)_m\underset{(CH_2)_n}{\overset{R^4}{\diagdown}}N—R^{3a}$$

wherein
A, m, n, R$^{3a}$ and R$^4$ are each as defined above;
R$^{2c}$ is a group of formula:

$$—(A)_m\underset{(CH_2)_n}{\overset{R^4}{\diagdown}}N—R^{3b}$$

wherein
A, m, n and R$^4$ are each as defined above and R$^{3b}$ is hydrogen;

R$^{2d}$ is a group of formula:

$$—(A)_m\underset{(CH_2)_n}{\overset{R^4}{\diagdown}}N—R^{3c}$$

wherein
A, m, n and R$^4$ are each as defined above and R$^{3c}$ is lower alkyl;
R$^{2e}$ is a group of formula:

$$—(A)_m\underset{(CH_2)_n}{\overset{R^4}{\diagdown}}N—R^{3c}$$

wherein
A, m, n, R$^{3c}$ and R$^4$ are each as defined above, or a group of formula:

$$\underset{}{\diagdown}N^+\underset{R^6}{\overset{R^5}{\diagup}}$$

wherein
R$^5$ and R$^6$ are each as defined above; and
X is a leaving group.

In addition to the processes as mentioned above, the object compound (I) and a salt thereof can be prepared, for example, according to the procedures as illustrated in Examples in the present specification or in a manner similar thereto.

The starting compounds can be prepared, for example, according to the procedures as illustrated in Preparations in the present specification or in a manner similar thereto.

The object compound (I) and a salt thereof can be prepared according to the methods as shown in Preparations or Examples, or in a manner similar thereto.

It is to be noted that the object compound (I) may include the geometrical isomer(s) due to the double bond(s) and/or the stereo isomer(s) due to the asymmetric carbon atom(s). In this regard, one isomer can be converted to another according to a conventional method in this field of the art.

It is also to be noted that the solvating form of the compound (I) (e.g. hydrate, etc.) and any form of the crystal of the compound (I) are included within the scope of the present invention.

Suitable salts of the object compound (I) are conventional pharmaceutically acceptable ones and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, trifluoroacetate, maleate, tartrate, fumarate, methanesulfonate, benzenesulfonate, formate, toluenesulfonate, etc.), an inorganic acid salt (e.g. hydrochloride, hydrobromide, hydroiodide, sulfate, phosphate, etc.), a salt with an amino acid (e.g. arginine, aspartic acid, glutamic acid, etc.), and the like.

Suitable examples and illustrations of the various definitions which the present invention includes within the scope thereof and which appear in the above and following description in the present specification are explained in detail as follows.

The term "lower" is intended to mean 1 to 6 carbon atom(s) unless otherwise indicated.

Suitable "lower alkyl" may include straight or branched ones such as methyl, ethyl, propyl, isopropyl, butyl, tert-butyl, pentyl, hexyl or the like, in which the preferred one may be ($C_1$–$C_4$) alkyl and the more preferred one may be methyl.

Suitable "unsaturated 3 to 8-membered heteromonocyclic group containing 1 or 2 sulfur atom(s) and 1 to 3 nitrogen atom(s)", which group may have 1 to 3 substituent(s) (e.g. lower alkyl, etc.), may include thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, and the like, in which the preferred one may be 5 or 6-membered one, and the more preferred one may be thiazolyl.

Suitable "acyl" may include lower alkanoyl (e.g. formyl, acetyl, propionyl, butyryl, isobutyryl, pivaloyl, hexanoyl, etc.); carboxy; protected carboxy; hydroxysulfonyl; and the like.

Suitable "protected carboxy" may be (1) an esterified carboxy, in which concrete examples may be the ones such as lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, 1-cyclopropylethoxycarbonyl, etc.) which may have substituent(s), for example, lower alkanoyloxy(lower) alkoxycarbonyl [e.g. acetoxymethoxycarbonyl, propionyloxymethoxycarbonyl, butyryloxymethoxycarbonyl, valeryloxymethoxycarbonyl, pivaloyloxymethoxycarbonyl, 1-acetoxyethoxycarbonyl, 1-propionyloxyethoxycarbonyl, pivaloyloxymethoxycarbonyl, 2-propionyloxyethoxycarbonyl, hexanoyloxymethoxycarbonyl, etc.]; lower alkanesulfonyl(lower)alkoxycarbonyl [e.g. 2-mesylethoxycarbonyl, etc.];

mono(or di or tri)halo(lower)alkoxycarbonyl [e.g. 2-iodoethoxycarbonyl, 2,2,2-trichloroethoxycarbonyl, etc.]; lower alkenyloxycarbonyl [e.g. vinyloxycarbonyl, allyloxycarbonyl, etc.];

lower alkynyloxycarbonyl [e.g. ethynyloxycarbonyl, propynyloxycarbonyl, etc.];

ar(lower)alkoxycarbonyl [preferably mono-(or di- or tri-) phenyl(lower)alkoxycarbonyl] which may have substituent(s) [e.g. benzyloxycarbonyl, 4-methoxybenzyloxycarbonyl, 4-nitro-benzyloxycarbonyl, phenethyloxycarbonyl, trityloxycarbonyl, benzhydryloxycarbonyl, bis(methoxyphenyl)methoxycarbonyl, 3,4-dimethoxybenzyloxycarbonyl, 4-hydroxy-3,5-di-tert-butylbenzyloxycarbonyl, etc.];

aryloxycarbonyl which may have substituent(s) [e.g. phenoxycarbonyl, 4-chlorophenoxycarbonyl, tolyloxycarbonyl, 4-tert-butylphenoxycarbonyl, xylyloxycarbonyl, mesityloxycarbonyl, cumenyloxycarbonyl, etc.] or the like;

(2) amidated carboxy, in which concrete examples may be carbamoyl;

N-(lower)alkylcarbamoyl (e.g. N-methylcarbamoyl, N-ethylcarbamoyl, N-isopropylcarbamoyl, N-butylcarbamoyl, N-pentylcarbamoyl, N-hexylcarbamoyl, etc.);

N-(higher)alkylcarbamoyl (e.g. N-heptylcarbamoyl, N-(2-methylheptyl)carbamoyl, N-nonylcarbamoyl, N-decanylcarbamoyl, N-tricyclo[3.3.1$^{3.7}$decanylcarbamoyl, N-undecanylcarbamoyl, N-(bicyclo[4.3.2]undecanyl)carbamoyl, N-dodecanylcarbamoyl, N-tridecanylcarbamoyl, N-tetradecanylcarbamoyl, N-pentadecanylcarbamoyl, N-hexadecanylcarbamoyl, N-heptadecanylcarbamoyl, N-octadecanylcarbamoyl, N-nonadecanylcarbamoyl, N-icosanylcarbamoyl, etc.);

N,N-di(lower)alkylcarbamoyl [e.g. N,N-dimethylcarbamoyl, N,N-diethylcarbamoyl, N-methyl-N-ethylcarbamoyl, N,N-dipropylcarbamoyl, N,N-di(tert-butyl)carbamoyl, N-pentyl-N-hexylcarbamoyl, etc.];

N-lower alkyl-N-ar(lower)alkylcarbamoyl (e.g. N-methyl-N-benzylcarbamoyl, etc.);

N-carboxy(lower)alkylcarbamoyl [e.g. N-carboxymethylcarbamoyl, N-(2-carboxyethyl)carbamoyl, N-(2-carboxypropyl)carbamoyl, N-(3-carboxypropyl)carbamoyl, N-(1-carboxymethylethyl)carbamoyl, N-(4-carboxybutyl)carbamoyl, N-(2-carboxymethyl-2-methylethyl)carbamoyl, N-(5-carboxypentyl)carbamoyl, N-(3-carboxyhexyl)carbamoyl, etc.];

N-protected carboxy(lower)alkylcarbamoyl, in which the preferred one may be N-esterified carboxy(lower) alkylcarbamoyl, and the more preferred one may be N-lower alkoxycarbonyl(lower)alkylcarbamoyl [e.g. N-(methoxycarbonylmethyl)carbamoyl, N-(ethoxycarbonylmethyl)carbamoyl, N-(2-ethoxycarbonylethyl)carbamoyl, N-(2-tert-butoxycarbonylethyl)carbamoyl, N-(3-methoxycarbonylpropyl)carbamoyl, N-(1-propoxycarbonylpropyl)carbamoyl, N-(1-isopropoxycarbonylmethylethyl)carbamoyl, N-(butoxycarbonylmethyl)carbamoyl, N-(tert-butoxycarbonylmethyl)carbamoyl, N-(4-isobutoxycarbonylbutyl)carbamoyl, N-(2-tert-butoxycarbonylmethyl-2-methylethyl)carbamoyl, N-(3-pentyloxycarbonylpentyl)carbamoyl, N-(6-hexyloxycarbonylhexyl)carbamoyl, N-[(1-cyclopropylethoxy)carbonylmethyl carbamoyl, etc.];

N-lower alkyl-N-carboxy(lower)alkylcarbamoyl [e.g. N-methyl-N-(carboxymethyl)carbamoyl, N-methyl-N-(2-carboxyethyl)carbamoyl, N-ethyl-N-(2-carboxypropyl)carbamoyl, N-propyl-N-(3-carboxypropyl)carbamoyl, N-isopropyl-N-(1-carboxymethylethyl)carbamoyl, N-butyl-N-(4-carboxybutyl)carbamoyl, N-tert-butyl-N-(2-carboxymethyl-2-methylethyl)carbamoyl, N-pentyl-N-(5-carboxypentyl)carbamoyl, N-hexyl-N-(3-carboxyhexyl)carbamoyl, etc.];

N-lower alkyl-N-protected carboxy(lower) alkylcarbamoyl, in which the preferred one may be N-lower alkyl-N-esterified carboxy(lower) alkylcarbamoyl, and the more preferred one may be N-lower alkyl-N-lower alkoxycarbonyl(lower) alkylcarbamoyl [e.g. N-methyl-N-(methoxycarbonylmethyl)carbamoyl, N-methyl-N-(ethoxycarbonylmethyl)carbamoyl, N-methyl-N-(2-ethoxycarbonylethyl)carbamoyl, N-ethyl-N-(2-tert-butoxycarbonylethyl)carbamoyl, N-propyl-N-(3- methoxycarbonylpropyl)carbamoyl, N-isopropyl-N-(1-propoxycarbonylpropyl)carbamoyl, N-propyl-N-(1-isopropoxycarbonylmethylethyl)carbamoyl, N-butyl-N-(butoxycarbonylmethyl)carbamoyl, N-isobutyl-N-(tert-butoxycarbonylmethyl)carbamoyl, N-butyl-N-(4-isobutoxycarbonylbutyl)carbamoyl, N-methyl-N-(2-tert-butoxycarbonylmethyl-2-methylethyl)carbamoyl, N-pentyl-N-(3-pentyloxycarbonylpentyl)carbamoyl, N-hexyl-N-(6-hexyloxycarbonylhexyl)carbamoyl, N-ethyl-N-[(1-cyclopropylethoxy)carbonylmethyl]carbamoyl, etc.];

N-hydroxy(lower)alkylcarbamoyl [e.g. N-hydroxymethylcarbamoyl, N-(2-hydroxyethyl)carbamoyl, N-(1-hydroxyethyl)carbamoyl, N-(3-hydroxypropyl)carbamoyl, N-(1-hydroxybutyl)carbamoyl, N-(2-hydroxymethyl-2-methylethyl)carbamoyl, N-(5-hydroxypentyl)carbamoyl, N-(3-hydroxyhexyl)carbamoyl, etc.]; a group of the formula:

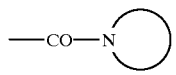

wherein a group of the formula:

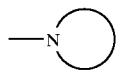

is N-containing heterocyclic group which may have one or more substituent(s), in which N-containing heterocyclic group may contain hetero atom(s) such as N, O or S in its ring; or the like; or the like.

Suitable example of the aforesaid "N-containing heterocyclic group" may include saturated or unsaturated, monocyclic or polycyclic heterocyclic group such as unsaturated 3 to 8-membered (more preferably 5 to 7-membered) heteromonocyclic group containing 1 to 4 nitrogen atom(s), for example, azepinyl (e.g. 1H-azepinyl, etc.), pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.) etc.;

saturated 3 to 8-membered (more preferably 5 to 7-membered) heteromonocyclic group containing 1 to 4 nitrogen atom(s), for example, perhydroazepinyl (e.g. perhydro-1H-azepinyl, etc.), pyrrolidinyl, imidazolidinyl, piperidino, piperazinyl, etc.;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;

saturated condensed heterocyclic group containing 1 to 4 nitrogen atom(s), for example, 7-azabicyclo[2.2.1]heptyl, 3-azabicyclo[3.2.2]nonanyl, etc.;

unsaturated 3 to 8-membered (more preferably 5 or 6-membered) heteromonocyclic group containing 1 or 2 oxygen atom(s) and 1 to 3 nitrogen atom(s), for example, dihydrooxazinyl (e.g. 5,6-dihydro-4H-dihydro-1,3-oxazinyl, etc.), oxazolyl, isoxazolyl, oxadiazolyl (e.g. 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 or 2 oxygen atom(s) and 1 to 3 nitrogen atom(s), for example, morpholinyl, sydnonyl, etc.;

unsaturated condensed heterocyclic group containing 1 or 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 or 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 or 2 sulfur atom(s) and 1 to 3 nitrogen atom(s), for example, thiazolidinyl, thiomorpholinyl, etc.;

unsaturated condensed heterocyclic group containing 1 or 2 sulfur atom(s) and 1 to 3 nitrogen atom(s), for example, benzothiazolyl, benzothiadiazolyl, etc.;

in which the preferred one may include saturated 3 to 8-membered heteromonocyclic group containing 1 to 4 nitrogen atom(s), saturated 3 to 8-membered heteromonocyclic group containing 1 or 2 oxygen atom(s) and 1 to 3 nitrogen atom(s); and saturated 3 to 8-membered heteromonocyclic group containing 1 or 2 sulfur atom(s) and 1 to 3 nitrogen atom(s).

The "N-containing heterocyclic group" thus defined may have one or more (preferably 1 to 3) substituent(s) such as lower alkyl as mentioned above;

hydroxy(lower)alkyl (e.g. hydroxymethyl, 1-hydroxyethyl, 2-hydroxyethyl, 3-hydroxypropyl, 2-hydroxybutyl, 1-methyl-1-hydroxymethylethyl, 4-hydroxypentyl, 3-hydroxyhexyl, etc.);

lower alkoxy(lower)alkyl (e.g. methoxymethyl, 2-methoxyethyl, 1-ethoxyethyl, 3-propoxypropyl, 2-(tert-butoxy)butyl, 5-pentyloxypentyl, 3-hexyloxyhexyl, etc.);

acyloxy(lower)alkyl such as lower alkanoyloxy(lower)alkyl (e.g. acetoxymethyl, 1-acetoxyethyl, 2-acetoxyethyl, 2-propionyloxyethyl, 3-propionyloxypropyl, 2-butyryloxybutyl, 4-pivaloyloxypentyl, 6-hexanoyloxyhexyl, etc.) or the like;

protected carboxy such as lower alkoxycarbonyl as mentioned above; carboxy; ar(lower)alkyl such as phenyl(lower)alkyl (e.g. benzyl, phenethyl, etc.), diphenyl(lower)alkyl (e.g. benzhydryl, etc.) or triphenyl(lower)alkyl (e.g. trityl, etc.); lower alkylamino (e.g. methylamino, ethylamino, propylamino, butylamino, tert-butylamino, pentylamino, hexylamino, etc.); acyl such as lower alkanoyl as mentioned above; or the like.

Suitable "aryl" may include phenyl, naphthyl, anthryl, and the like, in which the preferred one may be ($C_6$–$C_{10}$) aryl, and the more preferred one may be phenyl.

This "aryl" may have one or more (preferably 1 to 3) substituent(s) selected from the group consisting of halogen (e.g. fluoro, chloro, bromo, iodo), lower alkyl as mentioned above, lower alkoxy (e.g. methoxy, ethoxy, propoxy, butoxy, tert-butoxy, pentyloxy, hexyloxy, etc.), hydroxy, lower alkylsilyloxy (e.g. trimethylsilyloxy, tert-butyldimethylsilyloxy, etc.), phenyl(lower)alkoxy (e.g. phenylmethoxy, phenylethoxy, phenylpropoxy, phenylbutoxy, phenylpentyloxy, phenylhexyloxy, etc.), phenyl which may have halo(lower)alkyl (e.g. trifluoromethylphenyl, etc.), and the like.

Suitable "ar(lower)alkyl" may include phenyl(lower)alkyl (e.g. benzyl, phenethyl, etc.), diphenyl(lower)alkyl (e.g. benzhydryl, etc.) or triphenyl(lower)alkyl (e.g. trityl, etc.) and the like, in which the preferred one may be phenyl(lower)alkyl, and the more preferred one may be phenyl ($C_1$–$C_4$) alkyl.

This "ar(lower)alkyl" may have one or more (preferably 1 to 3) substituent(s) such as lower alkoxy as mentioned above, and the like.

Suitable "lower alkylene" may include straight or branched ones such as methylene, ethylene, trimethylene, propylene, tetramethylene, pentamethylene, hexamethylene, and the like, in which the preferred one may be ($C_1$–$C_4$) alkylene, and the more preferred ones are methylene and ethylene.

Suitable "a leaving group" may include halogen as mentioned above, hydroxy, acyloxy such as alkanoyloxy (e.g. acetoxy, propionyloxy, etc.), sulfonyloxy (e.g. mesyloxy, tosyloxy, etc.), and the like.

Of the object pyrazolopyridine compounds (I), (1) the preferred one may be the compound (I) wherein
$R^1$ is phenyl, and
$R^2$ is lower alkyl substituted with thiazolyl which may have 1 to 3 lower alkyl;
a group of the formula;

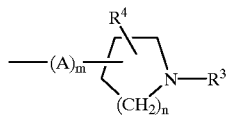

[wherein
$R^3$ is hydrogen, lower alkyl, phenyl(lower)alkyl, lower alkanoyl, lower alkoxycarbonyl, or phenyl(lower)alkoxycarbonyl,
$R^4$ is hydrogen or hydroxy,
A is lower alkylene,
m is an integer of 0 or 1, and
n is an integer of 1 or 2];
a group of the formula:

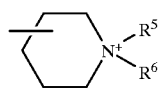

[wherein
$R^5$ and $R^6$ are each lower alkyl]; or quinuclidinyl, and (2) the more preferred one may be the compound (I) wherein
$R^1$ is phenyl, and
$R^2$ is lower alkyl substituted with thiazolyl which may have 1 to 3 lower alkyl, and (3) the most preferred one may be the compound (I) wherein
$R^1$ is phenyl, and
$R^2$ is a group of the formula:

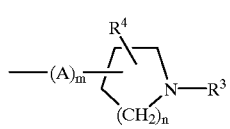

[wherein
$R^3$ is hydrogen, lower alkyl, phenyl(lower)alkyl, lower alkanoyl or lower alkoxycarbonyl, $R^4$ is hydrogen,
A is lower alkylene,
m is an integer of 0, and
n is an integer of 1 or 2], and (4) the most particularly preferred one may be the compound (I) wherein
$R^1$ is phenyl, and
$R^2$ is a group of the formula;

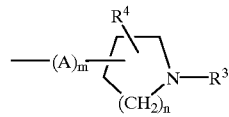

[wherein
$R^3$ is lower alkyl,
$R^4$ is hydrogen,
A is lower alkylene,
m is an integer of 0, and
n is an integer of 2].

The processes for the preparation of the object compound (I) and a salt thereof (Process 1 to 7) are explained in detail in the following.

Process 1

The compound (I) and a salt thereof can be prepared by reacting the compound (II) or a salt thereof with the compound (III) or a salt thereof.

Suitable salt of the compound (III) can be referred to the ones as exemplified for the compound (I).

The present reaction may be carried out in a solvent such as water, phosphate buffer, acetone, chloroform, acetonitrile, nitrobenzene, toluene, methylene chloride, ethylene chloride, formamide, N,N-dimethylformamide, methanol, ethanol, sec-butanol, amyl alcohol, diethyl ether, dimethoxyethane, dioxane, tetrahydrofuran, dimethyl sulfoxide, or any other organic solvent which does not adversely affect the reaction, preferably in ones having strong polarities. Among the solvents, hydrophillic solvents may be used in a mixture with water. When the compound (III) is in liquid, it can also be used as a solvent.

The reaction is preferably conducted in the presence of a base, for example, inorganic base such as alkali metal hydroxides alkali metal alkoxide, alkali metal carbonate, alkali metal bicarbonate, alkali metal hydride, organic base such as benzyltrimethylammonium hydroxide, trimethylamine, and the like.

The reaction temperature is not critical, and the reaction is usually carried out under cooling, at ambient temperature, under warming or under heating.

The present reaction is preferably carried out in the presence of alkali metal halide (e.g. sodium iodide, potassium iodide, etc.), alkali metal thiocyanate (e.g. sodium thiocyanate, potassium thiocyanate, etc.), di(lower)alkyl azodicarboxylate (e.g. diethyl azodicarboxylate, diisopropyl azodicarboxylate, etc.) or the like.

When X is —OH, activation of OH with triphenylphosphine and the like may be necessary.

Process 2

The compound (Ia) and a salt thereof can be prepared by reacting the compound (II) or a salt thereof with the compound (IV).

The reaction of this process can be carried out in a manner similar to that in Process 1.

Process 3

The compound (Ic) and a salt thereof can be prepared by subjecting the compound (Ib) or a salt thereof to elimination reaction of acyl.

Suitable salts of the compound (Ib) and (Ic) can be referred to the ones as exemplified for the compound (I).

This reaction is carried out in accordance with a conventional method such as hydrolysis.

The hydrolysis is preferably carried out in the presence of a base or an acid including Lewis acid. Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), picoline, 1,5-diazabicyclo[4,3,0]non-5-ene, 1,4-diazabicyclo[2,2,2] octane, 1,8-diazabicyclo[5,4,0]undec-7-ene, or the like.

Suitable acid may include an organic acid (e.g. formic acid, acetic acid, propionic acid, trichloroacetic acid, trifluoroacetic acid, etc.), and an inorganic acid (e.g. hydrochloric acid, hydrobromic acid, sulfuric acid, hydrogen chloride, hydrogen bromide, etc.). The elimination using Lewis acid such as trihaloacetic acid (e.g. trichloroacetic acid, trifluoroacetic acid, etc.) or the like is preferably carried out in the presence of cation trapping agents (e.g. anisole, phenol, etc.).

The reaction is usually carried out in a solvent such as water, an alcohol (e.g. methanol, ethanol, etc.), methylene chloride, tetrahydrofuran, dioxane, a mixture thereof or any other solvent which does not adversely influence the reaction. A liquid base or acid can be also used as the solvent.

The reaction temperature is not critical and the reaction is usually carried out under cooling to heating.

The reaction of this process can be also carried out according to a conventional reduction method employed in this field of the art (e.g. chemical reduction, catalytic reduction, etc.).

Process 4

The compound (Ic) and a salt thereof can be prepared by subjecting the compound (Id) or a salt thereof to dealkylation reaction.

Suitable salts of the compound (Ic) and (Id) can be referred to the ones as exemplified for the compound (I).

This reaction can be carried out by reacting the compound (Id) or a salt thereof with a dealkylating agent.

The dealkylating agent is halo(lower)alkyl haloformate and the like.

The reaction is usually carried out in a conventional solvent such as water, alcohol (e.g. methanol, ethanol, etc.), acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

The reaction temperature is not critical, and the reaction is usually carried out at ambient temperature, under warming or under heating.

Process 5

The compound (Ie) and a salt thereof can be prepared by subjecting the compound (Ic) or a salt thereof to alkylation reaction.

Suitable salts of the compound (Ic) and (Ie) can be referred to the ones as exemplified for the compound (I).

This reaction can be carried out by reacting the compound (Ic) or a salt thereof with an alkylating agent.

The alkylating agent is lower alkyl halide and the like.

The reaction is usually carried out in a conventional solvent such as water, alcohol (e.g. methanol, ethanol, etc.), acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

The reaction temperature is not critical, and the reaction is usually carried out at ambient temperature, under warming or under heating.

The present reaction is preferably carried out in the presence of alkali metal halide (e.g. sodium iodide, potassium iodide, etc.), alkali metal thiocyanate (e.g. sodium thiocyanate, potassium thiocyanate, etc.) or the like.

Process 6

The compound (Ib) and a salt thereof can be prepared by subjecting the compound (Ic) or a salt thereof to acylation reaction.

Suitable salts of the compound (Ib) and (Ic) can be referred to the ones as exemplified for the compound (I).

This reaction can be carried out by reacting the compound (Ic) or a salt thereof with an acylating agent.

The acylating agent is acyl halide corresponding to the acyl to be introduced, acyl anhydride corresponding to the acyl to be introduced, and the like.

The reaction is usually carried out in a conventional solvent such as water, alcohol (e.g. methanol, ethanol, etc.), acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

The reaction temperature is not critical, and the reaction is usually carried out at ambient temperature, under warming or under heating.

Process 7

The compound (If) and a salt thereof can be prepared by subjecting the compound (V) or a salt thereof to formation reaction of thiazole ring.

Suitable salts of the compound (V) and (If) can be referred to the ones as exemplified for the compound (I).

This reaction can be carried out by reacting the compound (V) or a salt thereof with a haloacetaldehyde or its reactive derivative.

The haloacetaldehyde or its reactive derivative is bromoacetaldehyde diethyl acetal, and the like.

The reaction is usually carried out in a conventional solvent such as water, alcohol (e.g. methanol, ethanol, etc.), acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

The reaction temperature is not critical, and the reaction is usually carried out at ambient temperature, under warming or under heating.

The object compound (I) of the present invention is an adenosine antagonist and possesses the various pharmacological actions as stated before.

In order to show the usefulness of the compound (I) of the present invention, the pharmacological test result of the representative compound of the present invention is shown in the following.

Test: Adenosine Antagonistic Activity

[I] Test Method

The adenosine antagonistic activity of the test compound was examined by radioligand binding techniques using 8-cyclopentyl-1,3-dipropylxanthine, dipropyl-2,3-$^3$H(N)] ($^3$H-DPCPX, 2×10$^{-9}$M) for human A$^1$ receptor.

[II] Test Compound

3-[2-(1-Methylpiperidin-4-yl)-3-oxo-2,3-dihydropyridazin-6-yl]-2-phenylpyrazolo[1,5-a]pyridine (the compound of Example 2)

[III] Test Result

The inhibition (%) was more than 90% at the dose of 1.0×10$^{-7}$ (M).

The pyrazolopyridine compound (I) and a salt thereof of this invention are usuful as adenosine antagonists and for the prevention and/or the treatment of depression, dementia (e.g. Alzheimer's disease, cerebrovascular dementia, Parkinson's disease, etc.), anxiety, pain, cerebrovascular disease (e.g. stroke, etc.), heart failure, and the like.

The pharmaceutical composition of this invention can be used in the form of a pharmaceutical preparation, for example, in a solid, semisolid or liquid form, which contains the pyrazolopyridine compound (I) or a pharmaceutically acceptable salt thereof as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation. The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. In addition, auxiliary, stabilizing agents, thickening agents, coloring agents and perfumes may be used where necessary. The pyrazolopyridine compound (I) or a pharmaceutically acceptable salt thereof is included in a pharmaceutical composition in an amount sufficient to produce the desired aforesaid pharmaceutical effect upon the process or condition of diseases.

For applying the composition to a human being or an animal, it is preferable to apply it by intravenous, intramuscular, pulmonary or oral administration, or insufflation. While the dosage of therapeutically effective amount of the pyrazolopyridine compound (I) varies depending on the age and condition of each individual patient to be treated, in the case of intravenous administration, a daily dose of 0.01–100 mg of the pyrazolopyridine compound (I) per kg weight of a human being or an animal, in the case of intramuscular administration, a daily dose of 0.1–100 mg of the pyrazolopyridine compound (I) per kg weight of a human being or an animal, and in case of oral administration, a daily dose of 0.5–100 mg of the pyrazolopyridine compound (I) per kg weight of a human being or an animal is generally given for the prevention and/or treatment of the aforesaid diseases.

The following Preparation and Examples are given for the purpose of illustrating the present invention in more detail.

Preparation 1

Into a mixture of 3-(2-cyanomethyl-3-oxo-2,3-dihydropyridazin-6-yl)-2-phenylpyrazolo[1,5-a]pyridine (2.0 g) and triethylamine (1.02 ml) in pyridine (10 ml) was introduced hydrogen sulfide at 50° C. for 6 hours. The mixture was poured into water. The resulting solid was collected by filtration to give 3-(3-oxo-2-thiocarbamoylmethyl-2,3-dihydropyridazin-6-yl)-2-phenylpyrazolo[1,5-a]pyridine (2.18 g).

mp: 220.0–221.0° C. (EtOH)

IR (Nujol): 3400, 3270, 3180, 1650, 1610, 1575 cm$^{-1}$

NMR (DMSO-d$_6$, δ): 5.03 (2H, s), 6.89 (1H, d, J=9.7 Hz), 7.03–7.08 (1H, m), 7.06 (1H, d, J=9.7 Hz), 7.36–7.50 (4H, m), 7.64–7.70 (2H, m), 8.04 (1H, d, J=8.9 Hz), 8.80 (1H, d, J=6.9 Hz), 9.42 (1H, s), 9.86 (1H, s).

(+)-APCI/MS (m/z): 362 (M+H)$^+$

Anal. Calcd. for $C_{19}H_{15}N_5OS·½H_2O$: C 61.61, H 4.35, N 18.91

Found: C 61.54, H 4.25, N 18.85

Preparation 2

To a solution of 4-piperidone hydrochloride (25 g) in a mixture of water (200 ml) and tetrahydrofuran (200 ml) was added dropwise benzyl chloroformate (29 ml) at 0 to 10° C., and the pH (pH 8.5–9.5) was adjusted with addition of 30% aqueous sodium hydroxide.

To the reaction mixture was added ethyl acetate (250 ml) and organic phase was separated, which was washed two times with 200 ml of saturated sodium chloride in water and dried over magnesium sulfate.

Evaporation of the solvent gave 1-benzyloxycarbonyl-4-piperidone (42.5 g, 98.8% yield).

NMR (CDCl$_3$, δ): 2.45 (4H, t, J=6.2 Hz), 3.79 (4H, t, J=6.3 Hz), 5.18 (2H, s), 7.36–7.40 (5H, m).

(+)-APCI/MS: 234 (M$^+$+1).

Preparation 3

To a suspension of sodium hydride (7.92 g, 60% dispersion in mineral oil) in dimethyl sulfoxide (250 ml) was added by portions trimethylsulfoxonium iodide (41.63 g) at room temperature under nitrogen atmosphere.

After stirring for 1 hour, to the reaction mixture was added dropwise 1-benzyloxycarbonyl-4-piperidone (42 g), and the mixture was heated to 55° C. and stirred for 4 hours.

The reaction mixture was poured into ice water (800 ml) and extracted three times with 800 ml of ethyl acetate.

Organic phase was combined, washed with water (500 ml×3) and saturated sodium chloride in water, and dried over magnesium sulfate.

Evaporation of the solvent gave a residue, which was chromatographed on silica gel eluting with 20% ethyl acetate in n-hexane to give 1-benzyloxycarbonylpiperidine-4-spiro-2'-oxirane (23.25 g, 52.2% yield).

NMR (CDCl$_3$, δ): 1.39–1.51 (2H, m), 1.76–1.91 (2H, m), 2.69 (2H, s), 3.41–3.55 (2H, m), 3.77–3.90 (2H, m), 5.15 (2H, s), 7.28–7.38 (5H, m).

(+)-APCI/MS: 248 (M$^+$+1)

Preparation 4

To a solution of (3R)-3-hydroxypyrrolidine hydrochloride (24.8 g) in a mixture of dioxane (200 ml) and water (200 ml) were added successively with triethylamine (60 ml) and di-tert-butyl dicarbonate (48.2 g) at 0° C., which mixture was allowed to warm to ambient temperature and stirred overnight.

Evaporation of the solvent gave a residue, which was dissolved in ethyl acetate (400 ml), washed successively with 1N aqueous hydrochloric acid (200 ml), saturated sodium hydrogencarbonate in water (200 ml) and saturated sodium chloride in water (200 ml×2), and dried over magnesium sulfate.

Insoluble material was removed by filtration and the filtrate was concentrated in vacuo to give (3R)-1-tert-butoxycarbonyl-3-hydroxypyrrolidine (27.17 g).

NMR (CDCl$_3$, δ): 1.46 (9H, s), 1.89–2.05 (2H, m), 2.77 (1H, s), 3.30–3.50 (4H, m), 4.39–4.47 (1H, m).

(+)-APCI/MS (m/z): 188 (M$^+$+1).

Preparation 5

1-tert-Butoxycarbonyl-4-piperidinol was obtained in 91.2% yield in substantially the same manner as in Preparation 4.

NMR (DMSO-d$_6$, δ): 1.14–1.33 (2H, m), 1.39 (9H, s), 1.60–1.74 (2H, m), 2.87–3.01 (2H, m), 3.55–3.71 (3H, m), 4.67 (1H, d, J=4.1 Hz).

Preparation 6

1-tert-Butoxycarbonyl-2-(2-hydroxyethyl)piperidine was obtained in substantially the same manner as in Preparation 4.

NMR (CDCl$_3$, δ): 1.40–2.05 (8H, m), 1.47 (9H, s), 2.60–2.80 (1H, m), 3.25–3.72 (2H, m), 3.75–4.05 (2H, m), 4.35–4.50 (1H, m).

Preparation 7

To a suspension of lithium aluminum hydride (2.0 g) in tetrahydrofuran (100 ml) was added dropwise a solution of 1-tert-butoxycarbonyl-2-(2-hydroxyethyl)piperidine (8.0 g) in tetrahydrofuran (50 ml) at ambient temperature under nitrogen atmosphere.

After stirring for 6 hours, the reaction mixture was refluxed for 3.5 hours.

The reaction mixture was allowed to cool to 5° C., and water (2 ml), 4N aqueous sodium hydroxide solution (2 ml) and water (6 ml) were successively added with care.

Insoluble material was removed by filtration and the filtrate was concentrated in vacuo to give a residue, which was chromatographed on silica gel eluting successively with chloroform, a mixture of chloroform and methanol (10:1) and methanol.

Fractions containing desired product were collected and the solvent was removed under reduced pressure to give 2-(2-hydroxyethyl)-1-methylpiperidine (2.47 g).

NMR (CDCl$_3$, δ): 1.20–1.85 (7H, m), 1.99–2.12 (2H, m), 2.20–2.35 (1H, m), 2.37 (3H,s), 2.85–2.95 (1H, m), 3.65–3.76 (1H, m), 3.90–4.04 (1H, m).

(+)-APCI/MS (m/z): 144 (M$^+$+1)

Preparation 8

To a suspension of 4-hydroxypiperidine (5.0 g) and triethylamine (7.6 ml) in dichloromethane (100 ml) was added dropwise propionyl chloride (4.5 ml) at −70 to −60° C. under nitrogen atmosphere.

After stirring for 1 hour, insoluble material was removed by filtration and the filtrate was concentrated in vacuo to give a residue, to which was added ethyl acetate (200 ml), followed by stirring for 30 minutes.

Insoluble material was removed by filtration and the filtrate was concentrated in vacuo to give 4-hydroxy-1-propionylpiperidine (7.70 g).

NMR (CDCl$_3$, δ): 1.15 (3H, t, J=7.5 Hz), 1.37–1.59 (2H, m), 1.82–1.96 (2H, m), 2.22 (2H, br-s), 2.36 (2H, q, J=7.5 Hz), 3.65–4.20 (3H, m).

(+)-AFCI/MS (m/z): 158 (M$^+$+1)

Preparation 9

To a suspension of lithium aluminum hydride (1.81 g) in tetrahydrofuran (100 ml) was added dropwise a solution of 4-hydroxy-1-propionylpiperidine (5.0 g) in tetrahydrofuran (30 ml) at ambient temperature under nitrogen atmosphere.

After stirring for 1 hours, the reaction mixture was refluxed for 4 hours, and then which was allowed to cool to 4° C.

To the resulting mixture were successively added with care water (1.81 ml), 4N aqueous sodium hydroxide solution (1.81 ml) and water (5.43 ml), which was followed by stirring for additional 1 hour.

Insoluble material was removed by filtration and the filtrate was concentrated in vacuo to give 4-hydroxy-1-propylpiperidine (4.37 g).

NMR (CDCl$_3$, δ): 0.89 (3H, t, J=7.4 Hz), 1.45–1.69 (4H, m), 1.84–2.19 (5H, m), 2.24–2.33 (2H, m), 2.73–2.84 (2H, m), 3.62–3.76 (1H, m).

(+)-APCI/MS (m/z): 144 (M$^+$+1)

Preparation 10

1-Butyryl-4-hydroxypiperidine was obtained in 98.7% yield in substantially the same manner as in Preparation 8.

NMR (CDCl$_3$, δ): 0.97 (3H, t, J=7.4 Hz), 1.40–1.75 (4H, m), 1.80–2.00 (2H, m), 2.27–2.36 (2H, m), 2.42 (1H, br-s), 3.10–3.30 (2H, m), 3.65–3.80 (1H, m), 3.85–3.98 (1H, m), 4.00–4.15 (1H, m).

(+)-APCI/MS (m/z): 172 (M$^+$+1)

Preparation 11

1-Butyl-4-hydroxypiperidine was obtained in 98.0% yield in substantially the same manner as in Preparation 9.

NMR (CDCl$_3$, δ): 0.91 (3H, t, J=7.2 Hz), 1.20–1.65 (6H, m), 1.80–2.20 (5H, m), 2.25–2.35 (2H, m), 2.70–2.80 (2H, m), 3.61–3.75 (1H, m).

(+)-APCI/MS (m/z): 158 (M$^+$+1)

Preparation 12

4-Hydroxy-1-pentanoylpiperidine was obtained in 98.3% yield in substantially the same manner as in Preparation 8.

NMR (CDCl$_3$, δ): 0.93 (3H, t, J=7.2 Hz), 1.20–1.70 (6H, m), 1.80–2.00 (2H, m), 2.25 (1H, br-s), 2.29–2.38 (2H, m), 3.09–3.27 (2H, m), 3.65–3.85 (1H, m), 3.86–4.00 (1H, m), 4.03–4.18 (1H, m).

(+)-APCI/MS (m/z): 186 (M$^+$+1)

Preparation 13

4-Hydroxy-1-pentylpiperidine was obtained in 99.4% yield in substantially the same manner as in Preparation 9.

NMR (CDCl$_3$, δ): 0.89 (3H, t, J=6.4 Hz), 1.20–1.65 (8H, m), 1.85–1.95 (2H, m), 2.00–2.35 (5H, m), 2.72–2.83 (2H, m), 3.50–3.75 (1H, m).

(+)-APCI/MS (m/z): 172 (M$^+$+1)

Preparation 14

1-Hexanoyl-4-hydroxypiperidine was obtained in 96.7% yield in substantially the same manner as in Preparation 8.

NMR (CDCl$_3$, δ): 0.90 (3H, t, J=6.6 Hz), 1.20–1.70 (8H, m), 1.78–2.00 (2H, m), 2.10 (1H, s), 2.28–2.37 (2H, m), 3.10–3.30 (2H, m), 3.65–3.82 (1H, m), 3.86–3.99 (1H, m), 4.03–4.20 (1H, m).

(+)-APCI/MS (m/z): 200 (M$^+$+1)

Preparation 15

1-Hexyl-4-hydroxypiperidine was obtained in 97.2% yield in substantially the same manner as in Preparation 9.

NMR (CDCl$_3$, δ): 0.88 (3H, t, J=6.6 Hz), 1.20–1.70 (10H, m), 1.80–1.95 (2H, m), 2.00–2.35 (5H, m), 2.70–2.85 (2H, m), 3.55–3.75 (1H, m).

(+)-APCI/MS (m/z): 186 (M$^+$+1)

Preparation 16

1-Acetylpiperidin-4-ol was obtained in 95.6% yield in substantially the same manner as in Preparation 8.

NMR (DMSO-d$_6$, δ): 1.10–1.40 (2H, m), 1.60–1.80 (2H, m), 1.97 (3H, s), 2.95 (1H, ddd, J=3.4 Hz, 9.6 Hz, 13.1 Hz), 3.05–3.19 (1H, m), 3.55–3.75 (2H, m), 3.80–3.95 (1H, m), 4.72 (1H, d, J=4.1 Hz).

(+)-APCI/MS (m/z): 144 (M$^+$+1)

Preparation 17

1-Ethylpiperidin-4-ol was obtained in 87.0% yield in substantially the same manner as in Preparation 9.

NMR (DMSO-d$_6$, δ): 0.96 (3H, t, J=7.2 Hz), 1.24–1.43 (2H, m), 1.60–1.75 (2H, m), 1.85–2.00 (2H, m), 2.26 (2H, q, J=7.2 Hz), 2.60–2.75 (2H, m), 3.33–3.50 (1H, m), 4.52 (1H, d, J=4.2 Hz).

(+)-APCI/MS (m/z): 130 (M$^+$+1)

Preparation 18

To a solution of isonipecotic acid (5 g) in a mixture of dioxane (50 ml) and water (25 ml) were successively added 38 ml of 1N aqueous sodium hydroxide solution and di-tert-butyl dicarbonate (8.87 g) at 0° C., which mixture was allowed to warm to ambient temperature and stirred overnight.

Evaporation of the solvent gave a residue, which was dissolved in ethyl acetate (200 ml) and water (100 ml).

The pH was adjusted to 2 with 2N aqueous hydrochloric acid. The organic phase was separated, and dried over magnesium sulfate.

Evaporation of the solvent gave 1-tert-butoxycarbonyl-4-piperidinecarboxylic acid (8.4 g).

NMR (DMSO-$d_6$, δ): 1.20–1.50 (2H, m), 1.39 (9H, s), 1.70–1.90 (2H, m), 2.30–2.50 (1H, m), 2.65–2.95 (2H, m), 3.83 (2H, br-d, J=13.2 Hz), 12.27 (1H, br-s).

Preparation 19

To a suspension of lithium aluminum hydride (350 mg) in tetrahydrofuran (20 ml) was added dropwise a solution of 1-tert-butoxycarbonyl-4-piperidinecarboxylic acid (1 g) at ambient temperature under nitrogen atmosphere.

After stirring for 24 hours, the reaction mixture was allowed to cool to 0° C., and water (0.35 ml), 4N aqueous sodium hydroxide solution (0.35 ml) and water (1.05 ml) were successively added with care.

Insoluble material was removed by filtration and the filtrate was concentrated in vacuo to give 1-m ethyl-4-piperidinemethanol (600 mg).

NMR (DMSO-$d_6$, δ): 1.00–1.80 (7H, m), 2.12 (3H, s), 2.72 (2H, br-d, J=11.5 Hz), 3.22 (2H, t, J=5.6 Hz), 4.40 (1H, t, J=5.3 Hz).

(+)-APCI/MS (m/z): 144 ($M^+$+1)

Preparation 20

To a stirred suspension of sodium hydride (238 mg) in tetrahydrofuran (50 ml) was added dropwise triethylphosphonoacetate (1.2 ml) at ambient temperature under nitrogen atmosphere.

After stirring for 30 minutes, to the reaction mixture was added dropwise 1-tert-butoxycarbonyl-4-piperidone (1 g), and the mixture was stirred overnight. To the stirred reaction mixture was added water (1 ml).

Evaporation of the solvent gave a residue, which was dissolved in ethyl acetate and washed successively with water (100 ml) and brine (100 ml), and dried over anhydrous magnesium sulfate.

Evaporation of the solvent gave a residue, which was chromatographed on silica gel eluting with a mixture of n-hexane and ethyl acetate (4:1) to give 1-tert-butoxycarbonyl-4-ethoxycarbonylmethylenepiperidine (1.19 g).

NMR (DMSO-$d_6$, δ): 1.17 (3H, t, J=7.1 Hz), 1.38 (9H, s), 2.20–2.30 (2H, m), 2.79–2.85 (2H, m), 3.34–3.44 (4H, m), 4.07 (2H, q, J=7.1 Hz), 5.75 (1H, s).

Preparation 21

A mixture of 1-tert-butoxycarbonyl-4-ethoxycarbonylmethylenepiperidine (3 g) and 10% palladium on carbon (50% wet, 600 mg) in methanol (150 ml) was stirred for 2 hours under hydrogen atmosphere.

The catalyst was removed by filtration. Evaporation of the solvent gave 1-tert-butoxycarbonyl-4-ethoxycarbonylmethylpiperidine (3.12 g).

NMR (DMSO-$d_6$, δ): 0.90–1.17 (2H, m), 1.17 (3H, t, J=7.1 Hz), 1.38 (9H, s), 1.55–1.95 (3H, m), 2.23 (2H, d, J=7.0 Hz), 2.55–2.85 (2H, m), 3.90 (2H, br-d, J=13.3 Hz), 4.05 (2H, q, J=7.1 Hz).

Preparation 22

1-Methyl-4-piperidineethanol was obtained in 82.0% yield in substantially the same manner as in Preparation 19.

NMR (DMSO-$d_6$, δ): 1.00–1.40 (5H, m), 1.58 (2H, br-d, J=12.4 Hz), 1.70–1.90 (2H, m), 2.10 (3H, s), 2.70 (2H, br-d, J=11.6 Hz), 3.41 (2H, q, J=6.5 Hz), 4.31 (1H, t, J=5.1 Hz).

(+)-APCI/MS (m/z): 130 ($M^+$+1)

EXAMPLE 1

A mixture of 3-(3-oxo-2-thiocarbamoylmethyl-2,3-dihydropyridazin-6-yl)-2-phenylpyrazolo[1,5-a]pyridine (0.50 g) and bromoacetaldehyde diethyl acetal (0.54 ml) in a mixture of methanol (2.5 ml) and chloroform (5 ml) was refluxed for 54 hours. After evaporating the solvent, the residue was chromatographed on silica gel (40 ml) using a mixture of chloroform and ethyl acetate (20:1). The desired fractions were collected and evaporated in vacuo. The residue was recrystallized from a mixture of ethyl acetate and n-hexane to give 3-[3-oxo-2-(2-thiazolylmethyl)-2,3-dihydropyridazin-6-yl]-2-phenylpyrazolo[1,5-a]pyridine (0.23 g) as yellow needles.

mp: 130.0–132.0° C. (EtOAc-n-hexane)

IR (Nujol): 1665, 1630, 1590, 1520 $cm^{-1}$

NMR (DMSO-$d_6$, δ): 5.68 (2H, s), 6.96 (1H, d, J=9.7 Hz), 7.08 (1H, dt, J=1.3 Hz, 6.9 Hz), 7.10 (1H, d, J=9.7 Hz), 7.37–7.49 (4H, m), 7.58–7.63 (2H, m), 7.75 (1H, d, J=3.3 Hz), 7.84 (1H, d, J=3.3 Hz), 7.89 (1H, d, J=8.9 Hz), 8.82 (1H, d, J=6.9 Hz).

(+)-APCI/MS (m/z): 386 $(M+H)^+$

Anal. Calcd. for $C_{21}H_{15}N_5OS \cdot \frac{1}{4}H_2O$: C 64.44, H 4.03, N 17.89

Found: C 64.05, H 3.85, N 17.57

EXAMPLE 2

A stirred mixture of 3-(3-oxo-2,3-dihydropyridazin-6-yl)-2-phenylpyrazolo[1,5-a]pyridine (2.0 g), 4-chloro-1-methylpiperidine hydrochloride (1.24 g) and sodium hydride (610 mg, 60% dispersion in mineral oil) in N,N-dimethylformamide (20 ml) was heated at 115° C., and stirred for 1 day.

The reaction mixture was cooled to ambient temperature and water was added thereto.

Evaporation of the solvent gave a residue, which was dissolved in chloroform (300 ml) and washed successively with water (20 ml×2), saturated sodium hydrogencarbonate in water (20 ml) and saturated sodium chloride in water (20 ml), and dried over magnesium sulfate.

Evaporation of the solvent gave a residue, which was chromatographed on silica gel (100 ml) eluting successively with chloroform and a mixture of chloroform and methanol (50:1→40:1→10:1). Fractions containing desired product were collected and the solvent was removed in vacuo to give a product, which was recrystallized from 50% aqueous ethanol to give 3-[2-(1-methylpiperidin-4-yl)-3-oxo-2,3-dihydropyridazin-6-yl]-2-phenylpyrazolo[1,5-a]pyridine (471 mg).

mp: 139.0–140.0° C. (aq. EtOH)

FT IR (KBr): 1660.4, 1589.1, 1531.2, 1496.5, 1465.6 $cm^{-1}$

NMR (DMSO-$d_6$, δ): 1.50–2.10 (6H, m), 2.20 (3H, s), 2.80–3.00 (2H, m), 4.70–4.90 (1H, m), 6.87 (1H, d, J=9.7 Hz), 7.05–7.13 (2H, m), 7.40–7:65 (6H, m), 7.90 (1H, d, J=8.9 Hz), 8.83 (1H, d, J=6.9 Hz).

(+)-APCI/MS (m/z): 386 (M+1)

Anal. Calcd. for $C_{23}H_{23}N_5O \cdot H_2O$: C 68.47, H 6.25, N 17.36

Found: C 68.71, H 6.08, N 17.37

EXAMPLE 3

To a stirred mixture of 3-(3-oxo-2,3-dihydropyridazin-6-yl)-2-phenylpyrazolo[1,5-a]pyridine (30 g), 1-methyl-4-hydroxypiperidine (15.58 g) and triphenylphosphine (40.94 g) in tetrahydrofuran (1.2 l) was added dropwise diethyl azodicarboxylate (24.58 ml) at −5 to 0° C. under nitrogen atmosphere.

The reaction mixture was allowed to warm to ambient temperature and stirred overnight.

Evaporation of the solvent gave a residue, which was dissolved in ethyl acetate (2 l) and extracted two times with 300 ml of 2N aqueous hydrochloric acid. Aqueous phases were combined and the pH was adjusted to 10.7 with 30% aqueous sodium hydroxide solution while keeping the temperature at 5 to 15° C.

Insoluble material was collected by filtration, washed with 500 ml of water and dried to give a crude product.

The crude product was dissolved in chloroform, which was chromatographed on silica gel (800 g) eluting successively with ethyl acetate, chloroform and a mixture of chloroform and methanol (40:1).

Fractions containing desired product were collected and the solvent was removed in vacuo to give crude crystals, which were recrystallized from 50% aqueous ethanol to give 3-[2-(1-methylpiperidin-4-yl)-3-oxo-2,3-dihydropyridazin-6-yl]-2-phenylpyrazolo[1,5-a]pyridine (19.36 g).

EXAMPLE 4

To a stirred solution of 3-(3-oxo-2,3-dihydropyridazin-6yl)- 2-phenylpyrazolo[1,5-a]pyridine (1.0 g), 1-methyl-4-hydroxypiperidine (520 mg) and triphenylphosphine (1.37 g) in tetrahydrofuran (40 ml) was added dropwise diisopropyl azodicarboxylate (1.03 ml) at −5 to 0° C. under nitrogen atmosphere.

The reaction mixture was allowed to warm to ambient temperature and stirred overnight.

Evaporation of the solvent gave a residue, which was dissolved in ethyl acetate (100 ml) and extracted two times with 50 ml of 6N aqueous hydrochloric acid. Aqueous phases were combined and the pH was adjusted to 10.0 with 30% aqueous sodium hydroxide solution while keeping the temperature at 5 to 15° C.

Insoluble material was collected by filtration, washed with water and dried under reduced pressure to give a crude product.

The crude product was dissolved in chloroform, which was chromatographed on silica gel (75 g) eluting with a mixture of chloroform and methanol (40:1).

Fractions containing desired product were collected and the solvent was removed in vacuo to give crude crystals, which were recrystallized from 50% aqueous ethanol to give 3-[2-(1-methylpiperidin-4-yl)-3-oxo-2,3-dihydropyridazin-6-yl]-2-phenylpyrazolo[1,5-a]pyridine (736 mg).

EXAMPLE 5

To a suspension of 3-[2-(1-methylpiperidin-4-yl)-3-oxo-2,3-dihydropyridazin-6-yl]-2-phenylpyrazolo[1,5-a]pyridine (5.7 g), in ethanol (30 ml) was added 25% hydrochloric acid in ethanol (5 ml), which mixture was stirred overnight at ambient temperature.

Resulting precipitates were collected by filtration, washed with ethanol and dried under reduced pressure to give 3-[2-(1-methylpiperidin-4-yl)-3-oxo-2,3-dihydropyridazin-6-yl]-2-phenylpyzazolo[1,5-a]pyridine hydrochloride (5.77 g).

mp: 271.0–274.0° C. (EtOH)

FT IR (KBr): 1658.5, 1587.1, 1525.4, 1490.7, 1467.6, 1419.4 cm$^{-1}$

NMR (DMSO-d$_6$, δ): 2.00–2.15 (2H, m), 2.25–2.45 (2H, m), 2.76 (3H, s), 3.15–3.35 (2H, m), 3.45–3.60 (2H, m), 5.05–5.25 (1H, m), 6.89 (1H, d, J=9.7 Hz), 7.04–7.14 (2H, m), 7.47–7.64 (6H, m), 8.10 (1H, d, J=8.9 Hz), 8.83 (1H, d, J=6.9 Hz), 10.72 (1H, br-s).

(+)FAB-MS (m/z): 386 (M$^+$+1)

Anal: Calcd. for $C_{23}H_{25}ClN_5O.3/2\ H_2O$ C: 61.53, H: 6.06, N: 15.60

Found: C: 61.39, H: 5.98, N: 15.60

EXAMPLE 6

3-[2-(1-tert-Butoxycarbonylpiperidin-4-yl)-3-oxo-2,3-dihydropyridazin-6-yl]-2-phenylpyrazolo[1,5-a]pyridine was obtained in 45.9% yield in substantially the same manner as in Example 3.

mp: 152.0–153.0° C. (EtOH)

FT IR (KBr): 1675.8, 1660.4, 1589.1, 1529.3, 1469.5, 1417.4 cm$^{-1}$

NMR (DMSO-d$_6$, δ): 1.41(9H, s), 1.60–1.90 (4H, m), 2.80–3.05 (2H, m), 4.00–4.15 (2H, m), 4.95–5.15 (1H, m), 6.91 (1H, d, J=9.7 Hz), 7.08 (1H, dt, J=1.3 Hz and 6.9 Hz), 7.18 (1H, d, J=9.7 Hz), 7.35–7.55 (4H, m), 7.56–7.62 (2H, m), 7.85 (1H, d, J=8.9 Hz), 8.83 (1H, d, J=6.9 Hz).

Anal: Calcd. for $C_{27}H_{29}N_5O_3.H_2O$ C: 66.24, H: 6.38, N: 14.30

Found: C: 66.66, H: 6.26, N: 14.24

EXAMPLE 7

A mixture of 3-[2-((3S)-1-tert-butoxycarbonylpyrrolidin-3-yl)-3-oxo-2,3-dihydropyridazin-6-yl]-2-phenylpyrazolo[1,5-a]-pyridine (2.4 g) in 6N-aqueous hydrochloric acid (50 ml) was refluxed for 4.5 hours.

The reaction mixture was cooled and the solvent was removed in vacuo.

To the resultant residue were added ethanol (15 ml) and 25% hydrochloric acid in ethanol (5 ml), which mixture was stirred overnight at ambient temperature.

Resulting precipitates were collected by filtration, washed with ethanol and dried under reduced pressure to give 3-[3-oxo-2-((3S)-pyrrolidin-3-yl)-2,3-dihydropyridazin-6-yl]-2-phenylpyrazolo[1,5-a]pyridine hydrochloride (1.8 g).

mp: 211.0–212.5° C. (EtOH)

FT IR (KBr): 1662.3, 1589.1, 1519.6, 1492.6, 1465.6, 1413.6 cm$^{-1}$

NMR (DMSO-d$_6$, δ): 2.20–2.40 (2H, m), 3.19–3.30 (2H, m), 3.41 (1H, dd, J=5.2 Hz and 12.3 Hz), 3.62 (1H, dd, J=7.6 Hz and 12.3 Hz), 5.56–5.65 (1H, m), 6.94 (1H, d, J=9.7 Hz), 7.09 (1H, dt, J=1.3 Hz and 6.9 Hz), 7.19 (1H, d, J=9.7 Hz), 7.41–7.52 (4H, m), 7.60–7.65 (2H, m), 7.93 (1H, d, J=8.9 Hz), 8.83 (1H, d, J=6.9 Hz), 9.46 (2H, br-s).

(+)-FAB/MS (m/z): 358 (M$^+$+1)

Anal. Calcd. for $C_{21}H_{20}ClN_5O.1¼H_2O$ C 60.58, H 5.45, N 16.82

Found: C 60.31, H 5.47, N 16.62

EXAMPLE 8

3-[3-Oxo-2-(piperidin-4-yl)-2,3-dihydropyridazin-6-yl]-2-phenylpyrazolo[1,5-a]pyridine hydrochloride was obtained in 79.5% yield in substantially the same manner as in Example 7.

mp: over 290° C. (EtOH)

FT IR (KBr): 1658.5, 1587.1, 1521.6, 1492.6, 1465.6, 1415.5 cm$^{-1}$

NMR (DMSO-d$_6$, δ): 1.95–2.40 (4H, m), 3.00–3.25 (2H, m), 3.30–3.45 (2H, m), 5.10–5.30 (1H, m), 6.89 (1H, d,

J=9.7 Hz), 7.05–7.15 (2H, m), 7.45–7.64(6H, m), 8.04 (1H, d, J=8.9 Hz), 8.83 (1H, d, J=6.9 Hz), 9.16 (2H, br-s).

(+)-FAB/MS (m/z): 372 (M$^+$+1)

Anal: Calcd. for C$_{22}$H$_{22}$ClN$_5$O.¾H$_2$O

C: 62.70, H: 5.62, N: 16.62

Found: C: 62.76, H: 5.72, N: 16.53

EXAMPLE 9

To a stirred mixture of 3-(3-oxo-2,3-dihydropyridazin-6-yl)-2-phenylpyrazolo[1,5-a]pyridine (3.34 g), (3R)-1-tertbutoxycarbonyl-3-hydroxypyrrolidine (2.6 g) and triphenylphosphine (4.55 g) in tetrahydrofuran (100 ml) was added dropwise diethyl azodicarboxylate (2.73 ml) at 0 to 5° C. under nitrogen atmosphere.

The reaction mixture was allowed to warm to ambient temperature and stirred overnight.

Evaporation of the solvent gave a residue, to which was added 6N aqueous hydrochloric acid (100 ml), and the mixture was refluxed for 8 hours.

The reaction mixture was cooled and washed with ethyl acetate (200 ml×2).

The pH of the aqueous phase was adjusted to 12 with 30% aqueous sodium hydroxide solution while keeping the temperature at 5 to 15° C.

The resultant was extracted with chloroform (200 ml×2) and organic phases were combined and dried over magnesium sulfate.

Evaporation of the solvent gave a residue, which was chromatographed on silica gel eluting successively with chloroform and a mixture of chloroform and methanol (40:1→20:1 →10:1).

Fractions containing desired product were collected and the solvent was removed in vacuo to give a crude product, which was recrystallized from ethanol to give 3-[3-oxo-2-((3S)-pyrrolidin-3-yl)-2,3-dihydropyridazin-6-yl]-2-phenylpyrazolo[1,5-a]pyridine (2.84 g).

mp: 144.0–145.5° C. (EtOH)

FT IR (KBr): 1658.5, 1585.2, 1525.4, 1490.7, 1465.6, 1415.5 cm$^{-1}$

NMR (DMSO-d$_6$, δ): 1.80–2.20 (2H, m), 2.75–3.00 (3H, m), 3.12 (1H, dd, J=7.2 Hz and 11.7 Hz), 5.37–5.47 (1H, m), 6.87 (1H, d, J=9.6 Hz), 7.07 (1H, dt, J=1.3 Hz and 6.9 Hz), 7.18 (1H, d, J=9.6 Hz), 7.40–7.62 (6H, m), 7.89 (1H, d, J=8.9 Hz), 8.82 (1H, d, J=6.9 Hz).

(+)-APCI/MS (m/z): 358 (M$^+$+1)

Anal. Calcd. for C$_{21}$H$_{19}$N$_5$O.⅔H$_2$O C 68.28, H 5.55, N 18.96

Found: C 68.47, H 5.28, N 18.90

EXAMPLE 10

3-[3-Oxo-2-(piperidin-4-yl)-2,3-dihydropyridazin-6-yl]-2-phenylpyrazolo[1,5-a]pyridine was obtained in 62.2% yield in substantially the same manner as in Example 9.

mp: 115.0–117.0° C. (aq. EtOH)

FT IR (KBr): 1656.6, 1585.2, 1529.3, 1494.6, 1463.7, 1421.3 cm$^{-1}$

NMR (DMSO-d$_6$, δ): 1.70–1.85 (4H, m), 2.50–2.70 (2H, m), 3.00–3.10 (2H, m), 4.80–5.00 (1H, m), 6.87 (1H, d, J=9.6 Hz), 7.05–7.13 (2H, m), 7.43–7.63(6H, m), 7.91 (1H, d, J=8.9 Hz), 8.82 (1H, d, J=6.9 Hz).

(+)-APCI/MS (m/z): 372 (M$^+$+1)

Anal: Calcd. for C$_{22}$H$_{21}$N$_5$O.2¼H$_2$O C: 64.21, H: 6.25, N: 17.02

Found: C: 64.26, H: 6.28, N: 16.94

EXAMPLE 11

3-[2-(1-Ethylpiperidin-4-yl)-3-oxo-2,3-dihydropyridazin-6-yl]-2-phenylpyrazolo[1,5-a]pyridine was obtained in 28.1% yield in substantially the same manner as in Example 3.

mp: 134.0–135.0° C. (50% aq. EtOH)

IR (KBr): 1660.4, 1589.1, 1529.3, 1492.6, 1465.6, 1415.5 cm$^{-1}$

NMR (DMSO-d$_6$, δ): 1.01 (3H, t, J=7.1 Hz), 1.80–2.15 (6H, m), 2.36 (2H, q, J=7.1 Hz), 2.90–3.10 (2H, m), 4.70–4.90 (1H, m), 6.87 (1H, d, J=9.7 Hz), 7.05–7.15 (2H, m), 7.45–7.60 (6H, m), 7.89 (1H, d, J=8.9 Hz), 8.83 (1H, d, J=6.9 Hz).

(+)-APCI/MS (m/z): 400 (M$^+$+1)

Anal. Calcd. for C$_{24}$H$_{25}$N$_5$O.¹⁄₁₀H$_2$O C: 70.57, H: 6.42, N: 17.14

Found: C: 71.02, H: 6.35, N: 17.07

EXAMPLE 12

3-[2-(1-Propylpiperidin-4-yl)-3-oxo-2,3-dihydropyridazin-6-yl]-2-phenylpyrazolo[1,5-a]pyridine was obtained in 44.7% yield in substantially the same manner as in Example 3.

mp: 104.0–106.0° C. (50% aq. EtOH)

IR (KBr): 1656.6, 1589.1, 1531.2, 1467.6, 1417.4, 1290.1 cm$^{-1}$

NMR (DMSO-d$_6$, δ): 0.86 (3H, t, J=7.3 Hz), 1.35–1.55 (2H, m), 1.70–2.35 (8H, m), 2.90–3.05 (2H, m), 4.70–4.90 (1H, m), 6.89 (1H, d, J=9.7 Hz), 7.05–7.30 (2H, m), 7.40–7.60 (6H, m), 7.88 (1H, d, J=8.9 Hz), 8.83 (1H, d, J=6.9 Hz).

(+)-APCI/MS (m/z): 414 (m$^+$+1)

Anal. Calcd. for C$_{25}$H$_{27}$N$_5$O.¹⁄₁₀H$_2$O C 72.58, H 6.60, N 16.86 found: C 72.61, H 6.58, N 16.94

EXAMPLE 13

3-[2-(1-Butylpiperidin-4-yl)-3-oxo-2,3-dihydropyridazin-6-yl]-2-phenylpyrazolo[1,5-a]pyridine was obtained in 44.6% yield in substantially the same manner as in Example 3.

mp: 106.0–108.0° C. (50% aq. EtOH)

IR (KBr): 1656.6, 1591.0, 1538.9, 1465.6, 1419.4, 1342.2 cm$^{-1}$

NMR (CDCl$_3$, δ): 0.94 (3H, t, J=7.1 Hz), 1.20–1.65 (4H, m), 1.90–2.50 (8H, m), 3.05–3.20 (2H, m), 4.95–5.15 (1H, m), 6.74 (1H, d, J=9.6 Hz), 6.88–6.96 (1H, m), 6.98 (1H, d, J=9.6 Hz), 7.28–7.40 (1H, m), 7.43–7.48 (3H, m), 7.55–7.62 (2H, m), 8.01 (1H, d, J=8.9 Hz), 8.52 (1H, d, J=6.9 Hz).

(+)-APCI/MS (m/z): 428 (M$^+$+1)

Anal. Calcd. for C$_{26}$H$_{29}$N$_5$O.½H$_2$O C 71.53, H 6.93, N 16.04 found: C 71.39, H 6.87, N 15.99

EXAMPLE 14

3-[3-Oxo-2-(1-pentylpiperidin-4-yl)-2,3-dihydropyridazin-6yl]-2-phenylpyrazolo[1,5-a]pyridine was obtained in 38.8% yield in substantially the same manner as in Example 3.

mp: 105.5–106.0° C. (aq. EtOH)

FT IR (KBr): 1660.4, 1589.1, 1531.2, 1496.5, 1465.6, 1417.4 cm$^{-1}$

NMR (DMSO-d$_6$, δ): 0.83–0.91 (3H, m), 1.20–1.45 (6H, m), 1.75–2.15 (6H, m), 2.20–2.35 (2H, m), 2.90–3.05 (2H, m), 4.70–4,90 (1H, m), 6.88 (1H, d, J=9.6 Hz), 7.05–7.15 (2H, m), 7.57–7.60 (2H, m), 7.88 (1H, d, J=8.9 Hz), 8.83 (1H, d, J=6.9 Hz).

(+)-APCI/MS (m/z): 442 (M$^+$+1)

Anal. Calcd. for C$_{27}$H$_{31}$N$_5$O.¼H$_2$O C 72.70, H 7.12, N 15.70 found: C 72.73, H 7.10, N 15.72

EXAMPLE 15

3-[2-(1-Hexylpiperidin-4-yl)-3-oxo-2,3-dihydropyridazin-6yl]-2-phenylpyrazolo[1,5-a]pyridine was obtained in 26.3% yield in substantially the same manner as in Example 3.

mp: 106.0–106.5° C. (aq. EtOH)

FT IR (KBr): 1660.4, 1589.1, 1531.2, 1463.7, 1417.4 cm$^{-1}$

NMR (DMSO-d$_6$, δ): 0.82–0.90 (3H, m), 1.20–1.55 (8H, m), 1.70–2.15 (6H, m), 2.20–2.35 (2H, m), 2.90–3.05 (2H, m), 4.70–4,90 (1H, m), 6.88 (1H, d, J=9.6 Hz), 7.00–7.15 (2H, m), 7.40–7.65 (6H, m), 7.88 (1H, d, J=8.9 Hz), 8.83 (1H, d, J=6.9 Hz).

(+)-APCI/MS (m/z): 456 (M$^+$+1)

Anal. Calcd. for C$_{28}$H$_{33}$N$_5$O.⅛H$_2$O C 73.45, H 7.32, N 15.30 found: C 73.35, H 7.39, N 15.28

EXAMPLE 16

To a suspension of sodium hydride (65 mg, 60% dispersion in mineral oil) in N,N'-dimethylformamide (20 ml) was added dropwise 3-[2-(piperidin-4-yl)-3-oxo-2,3-dihydropyridazin-6-yl]-2-phenylpyrazolo[1,5-a]pyridine (500 mg) at 25° C. under nitrogen atmosphere, which was followed by stirring for 30 minutes.

To the reaction mixture was added isopropyl iodide (940 mg) and the mixture was stirred for additional 18 hours.

To the resulting mixture were added excess triethylamine and water. Evaporation of the solvent gave a residue, which was dissolved in ethyl acetate (100 ml) and washed with 1N-aqueous hydrochloric acid. The aqueous layer was adjusted to pH 10–12 with 4N-aqueous sodium hydroxide solution and extracted with ethyl acetate (100 ml). The organic layer was separated, washed with water (100 ml) and dried over magnesium sulfate. Evaporation of the solvent gave a residue, which was recrystallized from 50% aqueous ethanol to give 3-[2-(1-isopropylpiperidin-4-yl)-3-oxo-2,3-dihydropyridazin-6-yl]-2-phenylpyrazolo[1,5-a]pyridine (350 mg).

mp: 157.5–158.3° C. (50% aq. EtOH)

IR (KBr): 1660.4, 1589.1, 1531.2, 1467.6, 1417.4 cm$^{-1}$

NMR (DMSO-d$_6$, δ): 0.98 (6H, d, J=6.5 Hz), 1.75–2.00 (4H, m), 2.20–2.40 (2H, m), 2.65–2.95 (3H, m), 4.70–4.90 (1H, m), 6.87 (1H, q, J=9.6 Hz), 7.05–7.13 (2H, m) 7.40–7.60 (6H, m), 7.88 (1H, d, J=8.9 Hz), 8.83 (1, d, J=7.0 Hz).

(+)-APCI/MS (m/z): 414 (M$^+$+1)

EXAMPLE 17

3-[2-(1-Methylpiperidin-3-yl)-3-oxo-2,3-dihydropyridazin-6-yl]-2-phenylpyrazolo[1,5-a]pyridine was obtained in 31.0% yield in substantially the same manner as in Example 3.

mp: 126.0–127.0°C. (50% aq. EtOH)

IR (KBr): 1658.5, 1587.1, 1529.3, 1465.6, 1417.4 cm$^{-1}$

NMR (DMSO-d$_6$, δ): 1.50–2.10 (6H, m), 2.18 (3H, s), 2.70–2.95 (2H, m), 4.80–5.00 (1H, m), 6.89 (1H, d, J=9.6 Hz), 7.00–7.15 (1H, m), 7.19 (1H, d, J=9.6 Hz), 7.40–7.65 (6H, m), 7.88 (1H, d, J=8.9 Hz), 8.82 (1H, d, J=6.9 Hz).

(+)-APCI/MS (m/z): 386.1 (M$^+$+1)

Anal. Calcd. for C$_{23}$H$_{23}$N$_5$O.1/2 H$_2$O C 65.54, H 6.46, N 16.61 found: C 65.75, H 6.39, N 16.56

EXAMPLE 18

3-[2-(1-Benzylpiperidin-4-yl)-3-oxo-2,3-dihydropyridazin-6-yl]-2-phenylpyrazolo[1,5-a]pyridine was obtained in 60.7% yield in substantially the same manner as in Example 3.

mp: 184.1–185.3° C. (50% aq. EtOH)

IR (KBr): 1662.3, 1589.1, 1525.4, 1490.7, 1459.8 1415.5 cm$^{-1}$

NMR (DMSO-d$_6$, δ): 1.70–2.20 (6H, m), 2.93 (2H, br-d, J=12.4 Hz), 3.51 (2H, s), 4.70–4.90 (1H, m), 6.88 (1H, d, J=9.6 Hz), 7.00–7.17 (2H, m), 7.20–7.65 (1H, m), 7.88 (1H, d, J=8.8 Hz), 8.84 (1H, d, J=7.0 Hz).

(+)-APCI/MS (m/z): 462 (M$^+$+1)

Anal. Calcd. for C$_{29}$H$_{27}$N$_5$O.½H$_2$O C 74.02, H 6.00, N 14.88 found: C 74.37, H 6.08, N 15.36

EXAMPLE 19

To a stirred solution of 3-(3-oxo-2-(piperidin-4-yl)-2,3-dihydropyridazin-6-yl)-2-phenylpyrazolo[1,5-a]pyridine (0.5 g) in pyridine (30 ml) was added dropwise acetic anhydride (1.28 ml) at ambient temperature.

The reaction mixture was stirred overnight.

Evaporation of the solvent gave a residue, which was dissolved in ethyl acetate (100 ml) and washed successively with 2N aqueous hydrochloric acid (100 ml) and saturated sodium chloride in water (100 ml), and dried over magnesium sulfate.

Insoluble material was removed by filtration. The filtrate was concentrated in vacuo to give 3-[2-(1-acetylpiperidin-4-yl)-3-oxo-2,3-dihydropyridazin-6-yl]-2-phenylpyrazolo[1,5-a]pyridine (0.5 g).

mp: 114.0–116.9° C. (EtOH)

IR (KBr): 1656.6, 1627.6, 1585.2, 1531.2, 1457.9, 1427.1 cm$^{-1}$

NMR (DMSO-d$_6$, δ): 1.50–2.00 (4H, m), 2.02 (3H, s), 2.60–2.80 (1H, m), 3.15–3.35 (1H, m), 3.90 (1H, br-d, J=12.2 Hz), 4.49 (1H, br-d, J=13.2 Hz), 5.00–5.20 (1H, m), 6.92 (1H, d, J=9.6 Hz), 7.03–7.12 (1H, m), 7.20 (1H, d, J=9.6 Hz), 7.40–7.60 (6H, m), 7.84 (1H, d, J=8.9 Hz), 8.83 (1H, d, J=6.9 Hz).

(+)-APCI/MS (m/z): 414 (M$^+$+1)

EXAMPLE 20

To a stirred mixture of 3-[3-oxo-2-(piperidin-4-yl)-2,3-dihydropyridazin-6-yl]-2-phenylpyrazolo[1,5-a]pyridine (500 mg), potassium tert-butoxide (182 mg) and 18-crown-6-ether (34 mg) in tetrahydrofuran (20 ml) was added methyl iodide (0.17 ml) at ambient temperature, which mixture was stirred overnight at that temperature.

An insoluble material appeared in the reaction mixture, which was collected by filtration. The crude solid was recrystallized from ethanol to give 3-[2-(1,1-dimethyl-4-piperidinio)-3-oxo-2,3-dihydropyridazin-6-yl]-2-phenylpyrazolo[1,5-a]pyridine iodide (730 mg).

mp: 225.0–226.5° C. (hexane)

IR (KBr): 1666.2, 1631.5, 1594.8, 1529.3, 1465.6 cm$^{-1}$

NMR (DMSO-d$_6$, δ): 1.95–2.30 (4H, m), 2.99 (3H, s), 3.17 (3H, s), 3.45–3.80 (4H, m), 5.00–5.20 (1H, m), 6.98 (1H, d, J=9.7 Hz), 7.06–7.14 (1H, m), 7.32 (1H, d, J=9.7Hz), 7.40–7.65 (6H, m), 7.91 (1H, d, J=8.9 Hz), 8.85 (1H, d, J=6.9 Hz).

(+)-APCI/MS (m/z): 400 (M$^+$)

EXAMPLE 21

3-[2-((3S)-1-tert-Butoxycarbonylpyrrolidin-3-yl)-3-dihydropyridazin-6-yl]-2-phenylpyrazolo[1,5-a]pyridine was obtained in 60.9% yield in substantially the same manner as in Example 3.

mp: 165.5–167.0° C. (EtOH)

FT IR (KBr): 1679.7, 1664.3, 1591.0, 1517.7, 1483.0, 1457.9, 1403.9 cm$^{-1}$

NMR (DMSO-d$_6$, δ): 1.30–1.40(9H, m), 2.10–2.30(2H, m), 3.34–3.80(4H, m), 5.45–5.60(1H, m), 6.89(1H, d, J=9.7 Hz), 7.04–7.11(1H, m), 7.13(1H, d, J=9.7 Hz), 7.34–7.64 (6H, m), 7.82(1H, d, J=8.9 Hz), 8.82(1H, d, J=6.9 Hz).

EXAMPLE 22

3-[3-Oxo-2-(3-quinuclidinyl)-2,3-dihydropyridazin-6-yl]-2-phenylpyrazolo[1,5-a]pyridine was obtained in 7.3% yield in substantially the same manner as in Example 3.

mp: 191.0–192.7° C. (50% aq. EtOH)

IR (KBr): 1660.4, 1591.0, 1535.1, 1467.6, 1411.6 cm$^{-1}$

NMR (CDCl$_3$, δ): 1.20–1.50 (1H, m), 1.55–2.00 (3H, m), 2.15–2.35 (1H, m), 2.70–3.20 (4H, m), 3.21–3.35 (1H, m), 3.59 (1H, dd, J=5.6 Hz and 13.9 Hz), 5.15–5.25 (1H, m), 6.80 (1H, d, J=9.6 Hz), 6.87–6.96 (1H, m), 7.07 (1H, d, J=9.6 Hz), 7.27–7.61 (6H, m), 7.91 (1H, d, J=8.9 Hz), 8.55 (1H, d, J=7.0 Hz).

(+)-APCI/MS (m/z): 398 (M$^+$+1)

EXAMPLE 23

3-[2-(1-Methylpiperidin-3-yl)methyl-3-oxo-2,3-dihydropyridazin-6-yl]-2-phenylpyrazolo[1,5-a]pyridine was obtained in 52.1% yield in substantially the same manner as in Example 3.

mp: 159.0–160.0° C. (50% aq. EtOH)

IR (KBr): 1658.5, 1587.1, 1529.3, 1465.6 cm$^{-1}$

NMR (DMSO-d$_6$, δ): 0.90–1.10 (1H, m), 1.30–2.00 (5H, m), 2.05–2.30 (1H, m), 2.13 (3H, s), 2.50–2.60 (2H, m), 3.94–4.15 (2H, m), 6.87 (1H, d, J=9.6 Hz), 7.03–7.13 (2H, m), 7.40–7.65 (6H, m), 7.92 (1H, d, J=8.9 Hz), 8.82 (1H, d, J=6.9 Hz).

Anal. Calcd. for C$_{24}$H$_{25}$N$_5$O.³⁄₁₀H$_2$O C 71.19, H 6.37, N 17.30

Found: C 71.40, H 6.34, N 17.30

(+)-APCI/MS (m/z): 400.2 (M$^+$+1)

EXAMPLE 24

3-[2-(1-Methylpiperidin-2-yl)methyl-3-oxo-2,3-dihydropyridazin-6-yl]-2-phenylpyrazolo[1,5-a]pyridine was obtained in 58.6% yield in substantially the same manner as in Example 3.

mp: 154.0–155.0° C. (50% aq. EtOH)

IR (KBr) 1662.3, 1587.1, 1527.3, 1498.4, 1463.7 cm$^{-1}$

NMR (DMSO-d$_6$, δ).1.10–1.70 (6H, m), 2.05–2.20 (1H, m), 2.29 (3H, s), 2.40–2.60 (1H, m), 2.70–2.85 (1H, m), 4.04 (1H, dd, J=4.7 Hz and 12.9 Hz), 4.44 (1H, dd, J=4.7 Hz and 12.9 Hz), 6.87 (1H, d, J=9.6 Hz), 7.00–7.15 (2H, m), 7.40–7.65 (6H, m), 7.98 (1H, d, J=8.9 Hz), 8.82 (1H, d, J=6.9 Hz).

(+)-APCI/MS (m/z): 400.2 (M$^+$+1)

Anal. Calcd. for C$_{24}$H$_{25}$N$_5$O C 72.16, H 6.31, N 17.53

Found: C 72.30, H 6.41, N 17.53

EXAMPLE 25

3-[2-{2-(1-Methylpiperidin-2-yl)ethyl}-3-oxo-2,3-dihydropyridazin-6-yl]-2-phenylpyrazolo[1,5-a]pyridine was obtained in 91.0% yield in substantially the same manner as in Example 3.

mp: 113.5–116.0° C. (EtOH-n-Hexane)

FT IR (KBr): 1666.2, 1633.4, 1589.1, 1527.3, 1496.5, 1463.7, 1419.4 cm$^{-1}$

NMR (DMSO-d$_6$, δ): 1.10–1.75 (6H, m), 1.80–2.05 (4H, m), 2.18 (3H, s), 2.76 (1H, br-d, J=11.4 Hz), 4.10–4.21 (2H, m), 6.87 (1H, d, J=9.6 Hz), 7.03–7.13 (1H, m), 7.12 (1H, d, J=9.6 Hz), 7.39–7.63 (6H, m), 7.94 (1H, d, J=8.9 Hz), 8.82 (1H, d, J=6.9 Hz).

(+)-APCI/MS (m/z): 414 (M$^+$+1)

Anal. Calcd. for C$_{25}$H$_{27}$N$_5$O.⅛H$_2$O C 72.22, H 6.61, N 16.84

Found: C 72.03, H 6.55, N 16.81

EXAMPLE 26

3-[3-Oxo-2-[2-(piperidin-2-yl)ethyl]-2,3-dihydropyridazin-6-yl]-2-phenylpyrazolo[1,5-a]pyridine was obtained in 33.3% yield in substantially the same manner as in Example 9.

mp: 124.4–125.4 (50% aq. EtOH)

IR (KBr): 1662.3, 1585.2, 1527.3, 1496.5, 1463.7, 1446.4, 1421.3 cm$^{-1}$

NMR (CDCl$_3$, δ): 1.15–2.20 (8H, m), 2.50–2.70 (2H, m), 3.13 (1H, br-d, J=12.0 Hz), 4.19–4.33 (1H, m), 4.40–4.55 (1H, m), 6.76 (1H, d, J=9.6 Hz), 6.90–6.97 (1H, m), 7.03 (1H, d, J=9.6 Hz), 7.30–7.65 (6H, m), 7.99 (1H, d, J=9.0 Hz), 8.54 (1H, d, J=6.9 Hz).

(+)-APCI/MS (m/z): 400 (M$^+$+1)

Anal. Calcd. for C$_{24}$H$_{25}$N$_5$O.H$_2$O C 69.04, H 6.52, N 16.77

Found: C 69.53, H 6.33, N 16.83

EXAMPLE 27

3-[2-(1-Methylpiperidin-4-yl)methyl-3-oxo-2,3-dihydropyridazin-6-yl]-2-phenylpyrazolo[1,5-a]pyridine was obtained in 7.9% yield in substantially the same manner as in Example 3.

mp: 179.5–181.0° C. (EtOH)

IR (KBr): 1656.6, 1587.1, 1525.4, 1490.7, 1450.2, 1419.4 cm$^{-1}$

NMR (DMSO-d$_6$, δ): 1.15–1.45 (2H, m), 1.50–1.65 (2H, m), 1.70–1.95 (3H, m), 2.14 (3H, s), 2.74 (2H, br-d, J=10.9 Hz), 4.02 (2H, d, J=7.1 Hz), 6.88 (2H, d, J=9.6 Hz), 7.00–7.20 (2H, m), 7.40–7.65 (6H, m), 7.90 (1H, d, J=8.9 Hz), 8.83 (1H, d, J=7.0 Hz).

(+)-APCI/MS (m/z): 400 (M$^+$1)

EXAMPLE 28

To a stirred mixture of 3-(3-oxo-2,3-dihydropyridazin-6-yl)-2-phenylpyrazolo[1,5-a]pyridine (2.7 g), 1-methyl-4-piperidineethanol (1.41 g) and triphenylphosphine (3.19 g) in tetrahydrofuran (60 ml) was added dropwise diethyl azodicarboxylate (1.92 ml) at 0 to 5° C. under nitrogen atmosphere.

The reaction mixture was allowed to warm to ambient temperature and stirred overnight.

Evaporation of the solvent gave a residue, to which was added 2N aqueous hydrochloric acid, and the mixture was under stirring for 1 hour.

The reaction mixture was washed with ethyl acetate.

Aqueous phase was separated. The pH of the aqueous phase was adjusted to 12 with 15% aqueous sodium hydroxide solution while keeping the temperature at 5 to 15° C. The resulting solution was extracted with ethyl acetate.

Organic phase was separated, washed with water and dried over magnesium sulfate.

Evaporation of the solvent gave a residue, which was added in ethanol (2 ml). 25% Hydrochloric acid in ethanol (1 ml) was added thereto and the mixture was stirred overnight.

Insoluble material was collected and washed with ethanol to give 3-[2-(1-methylpiperidin-4-yl)ethyl-3-oxo-2,3-dihydropyridazin-6-yl]-2-phenylpyrazolo[1,5-a]pyridine hydrochloride (2.93 g).

mp: over 250° C. (50% aq. EtOH)

IR (KBr): 1654.6, 1583.3, 1527.3, 1467.6, 1417.4 $cm^{-1}$

NMR (DMSO-$d_6$, δ): 1.30–2.00 (7H, m), 2.69 (3H, s), 2.75–3.00 (2H, m), 3.20–3.50 (2H, m), 4.17 (2H, t, J=6.8 Hz), 6.89 (1H, d, J=9.6 Hz), 7.05–7.18 (2H, m), 7.40–7.65 (6H, m), 7.92 (1H, d, J=8.9 Hz), 8.83 (1H, d, J=6.9 Hz).

(+)-APCI/MS (m/z): 414 ($M^{30}$ +1)

Anal. Calcd. for $C_{25}H_{28}ClN_5O \cdot \frac{1}{10}H_2O$ C 66.46, H 6.29, N 15.50

Found: C 66.18, H 6.34 N 15.34

EXAMPLE 29

To a stirred solution of 3-[2-(1-methylpiperidin-3-yl)-methyl)-3-oxo-2,3-dihydropyridazin-6-yl]-2-phenylpyrazolo[1,5-a]pyridine (300 mg) in 1,2-dichloroethane (50 ml) was added dropwise 1-chloroethyl chloroformate (324 μl).

The reaction mixture was refluxed under stirring for 16 hours.

Evaporation of the solvent gave a residue, which was dissolved in ethyl acetate (100 ml) and extracted with 100 ml of 2N aqueous hydrochloric acid. Aqueous phase was separated, and the pH was adjusted to 12 with 30% aqueous sodium hydroxide solution while keeping the temperature at 5 to 15° C.

This aqueous phase was extracted with ethyl acetate (100 ml). The organic phase was washed with saturated sodium chloride in water (100 ml), and dried over magnesium sulfate.

Evaporation of the solvent gave a crude product. The crude product was dissolved in chloroform, which solution was chromatographed on silica gel eluting with a mixture of chloroform and methanol (40:1).

Fractions containing desired product were collected and the solvent was removed in vacua to give a crude solid, which was recrystallized from 50% aqueous ethanol to give 3-[3-oxo-2-(piperidin-3-yl)methyl-2,3-dihydropyridazin-6-yl]-2 -phenylpyrazolo[1,5-a]pyridine (75 mg).

mp: 250.0–251.3° C. (EtOH)

IR (KBr): 1656.6, 1587.1, 1525.4, 1465.6, 1419.4 $cm^{-1}$

NMR (DMSO-$d_6$, δ): 1.20–1.80 (4H, m), 2.10–2.50 (1H, m), 2.55–2.80 (2H, m), 3.00–3.30 (3H, m), 4.08 (2H, d, J=7.1 Hz), 6.90 (1H, d, J=9.7 Hz), 7.00–7.15 (2H, m), 7.40–7.65 (6H, m), 7.95 (1H, d, J=8.9 Hz), 8.83 (1H, d, J=6.9 Hz).

(+)-APCI/MS (m/z): 386 ($M^+$+1)

EXAMPLE 30

3-[2-{(Piperidin-2-yl)methyl}-3-oxo-2,3-dihydropyridazin-6-yl]-2-phenylpyrazolo[1,5-a]pyridine was obtained in 17.3% yield in substantially the same manner as in Example 29.

mp: 141.0–142.5° C. (50% aq. EtOH)

IR (KBr): 1666.2, 1633.4, 1591.0, 1527.3, 1494.6 $cm^{-1}$

NMR (DMSO-$d_6$, δ): 0.86–1.80 (6H, m), 2.40–2.60 (1H, m), 2.90–3.10 (3H, m), 4.05 (2H, d, J=6.1 Hz), 6.87 (1H, d, J=9.6 Hz), 7.00–7.15 (2H, m), 7.40–7.65 (6H, m), 7.97 (1H, d, J=9.0 Hz), 8.82 (1H, d, J=6.9 Hz).

(+)-APCI/MS (m/z): 386 ($M^+$+1)

Anal. Calcd. for $C_{23}H_{23}N_5O \cdot \frac{1}{2}H_2O$ C 70.03, H 5.88, N 17.75

Found: C 70.31, H 6.12, N 18.19

EXAMPLE 31

3-[2-{((2S)-1-Methylpyrrolidin-2-yl)methyl}-3-oxo-2,3-dihydropyridazin-6-yl]-2-phenylpyrazolo[1,5-a]pyridine was obtained in 74.6% yield in substantially the same manner as in Example 3.

mp: 114.5–117.0° C. (n-Hexane-CHCl$_3$)

FT IR (KBr): 1664.3, 1635.3, 1589.1, 1529.3, 1496.5, 1463.7, 1423.2 $cm^{-1}$

NMR (DMSO-$d_6$, δ): 1.50–2.00 (4H, m), 2.15–2.30 (1H, m), 2.30 (3H, s), 2.60–2.80 (1H, m), 2.90–3.10 (1H, m), 4.05 (1H, dd, J=7.2 Hz and 12.7 Hz), 4.27 (1H, dd, J=4.6 Hz and 12.7 Hz), 6.88 (1H, d, J=9.6 Hz), 7.00–7.14 (2H, m), 7.40–7.60 (6H, m), 8.00 (1H, d, J=8.9 Hz), 8.83 (1H, d, J=6.9 Hz).

(+)-APCI/MS (m/z): 386 ($M^+$+1)

Anal. Calcd. for $C_{23}H_{23}N_5O \cdot \frac{1}{2}H_2O$ C 70.03, H 6.13, N 17.75

Found: C 70.06, H 5.97, N 17.67

EXAMPLE 32

3-[3-Oxo-2-((2S)-pyrrolydin-2-yl)methyl-2,3-dihydropyridazin-6-yl]-2-phenylpyrazolo[1,5-a]pyridine was obtained in 62.3% yield in substantially the same manner as in Example 9.

mp: 111.5–113.5° C. (50% aq. EtOH)

(KBr): 1662.3, 1633.4, 1589.1, 1529.3, 1496.5, 1467.6 $cm^{-1}$

NMR (DMSO-d$_6$, δ): 1.20–1.90 (4H, m), 2.70–3.00 (1H, m), 3.45–3.65 (1H, m), 4.05–4.10 (2H, m), 6.90 (1H, d, J=9.6 Hz), 7.00–7.15 (2H, m), 7.30–7.65 (6H, m), 8.02 (1H, d, J=8.9 Hz), 8.82 (1H, d, J=6.9 Hz).

(+)-APCI/MS (m/z): 372 (M$^+$+1)

Anal. Calcd. for C$_{22}$H$_{21}$N$_5$O.H$_2$O C 67.85, H 5.95, N 17.98

Found: C 68.21, H 5.73, N 17.64

EXAMPLE 33

To a solution of sodium hydroxide (300 mg) in a mixture of water (20 ml) and toluene (20 ml) were added successively 3-(3-oxo-2,3-dihydropyridazin-6-yl)-2-phenylpyrazolo[1,5-a]pyridine (1.94 g), benzyltriethylammonium chloride (155 mg) and 1-benzyloxycarbonylpiperidine-4-spiro-2'-oxirane (5 g), and the mixture was refluxed for 5 hours.

The reaction mixture was cooled and extracted with chloroform (200 ml). Organic phase was separated, which was washed successively with 1N-aqueous sodium hydroxide (20 ml) and saturated sodium chloride in water, and dried over magnesium sulfate.

Evaporation of the solvent gave a residue, which was chromatographed on silica gel (250 ml) eluting successively with 20% ethyl acetate in n-hexane and ethyl acetate.

Fractions containing desired product were collected and the solvent was removed under reduced pressure to give a crude product, which was recrystallized from ethanol to give 3-[2-(1-benzyloxycarbonyl-4-hydroxypiperidin-4-yl)methyl-3-oxo-2,3-dihydropyridazin-6-yl]-2-phenylpyrazolo[1,5-a]pyridine (2.8 g, 79.8% yield).

mp: 175.5–177.0° C. (EtOH)

FT IR (KBr): 1697.1, 1650.8, 1583.8, 1527.3, 1490.7, 1469.5 cm$^{-1}$

NMR (DMSO-d$_6$, δ): 1.42–1.60 (4H, m), 3.00–3.30 (2H, m), 3.70–3.90 (2H, m), 4.21 (2H, s), 4.95 (1H, s), 5.06 (1H, s), 6.89 (1H, d, J=9.6 Hz), 7.03–7.12 (2H, m), 7.28–7.64 (10H, m), 8.07 (1H, d, J=8.9 Hz), 8.81 (1H, d, J=6.9 Hz).

(+)-APCI/MS: 536 (M$^+$+1)

Anal. Calcd. for C$_{31}$H$_{29}$N$_5$O$_4$ C 69.52, H 5.46, N 13.08

Found: C 69.32, H 5.40, N 13.01

EXAMPLE 34

A mixture of 3-[2-(1-benzyloxycarbonyl-4-hydroxypiperidin-4-yl)methyl-3-oxo-2,3-dihydropyridazin-6-yl]-2-phenylpyrazolo-[1,5-a]pyridine (2.5 g), 10% palladium on carbon (500 mg, 50% wet) and concentrated hydrochloric acid (100 μl) in N,N-dimethylformamide (100 ml) was stirred under hydrogen atmosphere.

On confirmation of the absence of the starting material by TLC check, the catalyst was removed by filtration and to the filtrate was added triethylamine.

The solvent was removed under reduced pressure to give a residue, which was chromatographed on silica gel (100 ml) eluting successively with chloroform, 9% and 20% methanol in chloroform.

Fractions containing desired product were collected and concentrated in vacuo to give a crude product, which was recrystallized from ethanol to give 3-[2-(4-hydroxypiperidin-4-yl)methyl-3-oxo-2,3-dihydropyridazin-6-yl]-2-phenylpyrazolo[1,5-a]pyridine (817 mg, 42.6% yield).

mp: over 260° C. (EtOH)

FT IR (KBr): 1648.8, 1581.3, 1517.7, 1490.7 cm$^{-1}$

NMR (DMSO-d$_6$, δ): 1.60–1.90 (4H, m), 2.90–3.20 (4H, m), 4.24 (2H, s), 5.18 (1H, s), 6.90 (1H, d, J=9.6 Hz), 7.05–7.12 (2H, m), 7.39–7.63 (6H, m), 8.10 (1H, d, J=8.9 Hz), 8.83 (1H, d, J=6.9 Hz).

(+)-APCI/MS: 402 (M$^+$+1)

EXAMPLE 35

A mixture of 3-[2-(4-hydroxypiperidin-4-yl)methyl-3-oxo-2,3-dihydropyridazin-6-yl]-2-phenylpyrazolo[1,5-a]pyridine (650 mg) and acetic anhydride (1.53 ml) in pyridine (30 ml) was stirred overnight at room temperature.

Evaporation of the solvent gave a residue, which was dissolved in chloroform (150 ml) and washed succesively with 1N aqueous hydrochloric acid, saturated sodium hydrogencarbonate in water and saturated sodium chloride in water, and dried over magnesium sulfate.

Evaporation of the solvent gave a crude product, which was recrystallized from ethanol to give 3-[2-(1-acetyl-4-hydroxypiperidin-4-yl)methyl-3-oxo-2,3-dihydropyridazin-6-yl]-2-phenylpyrazolo[1,5-a]pyridine (284 mg, 39.6% yield).

mp: 163.0–165.0° C. (EtOH)

FT IR (KBr): 1646.9, 1581.3, 1527.3, 1490.7 cm$^{-1}$

NMR (DMSO-d$_6$, δ): 1.40–1.62 (4H, m), 1.97 (3H, s), 2.80–3.00 (1H, m), 3.20–3.40 (1H, m), 3.50–3.70 (1H, m), 4.00–4.20 (1H, m), 4.22 (2H, m), 4.93 (1H, s), 6.88 (1H, d, J=9.6 Hz), 7.05–7.10 (2H, m), 7.39–7.51 (4H, m), 7.58–7.62 (2H, m), 8.09 (1H, d, J=8.9 Hz), 8.81 (1H, d, J=6.9 Hz).

(+)-APCI/MS (m/z): 444 (M$^+$+1)

Anal. Calcd. for C$_{25}$H$_{25}$N$_5$O$_3$.H$_2$O C 65.06, H 5.90, N 15.17

Found: C 65.26, H 5.80, N 15.15

EXAMPLE 36

3-[2-(2-Methylthiazol-4-yl)methyl-3-oxo-2,3-dihydropyridazin-6-yl]-2-phenylpyrazolo[1,5-a]pyridine was obtained in 51.9% yield in substantially the same manner as in Example 3.

mp: 196.0–197.5° C. (EtOH)

FT IR (KBr): 1666.2, 1631.5, 1592.9, 1531.2, 1494.6, 1469.5, 1452.1, 1419.4 cm$^{-1}$

NMR (DMSO-d$_6$, δ): 2.67 (3H, s), 5.38 (2H, s), 6.89 (1H, d, J=9.6 Hz), 7.05 (1H, d, J=9.6 Hz), 7.05–7.10 (1H, m), 7.30–7.41 (2H, m), 7.45–7.50 (3H, m), 7.59–7.65 (2H, m), 7.85 (1H, d, J=8.9 Hz), 8.80 (1H, d, J=6.9 Hz).

(+)-APCI/MS (m/z): 400 (M$^+$+1)

Anal. Calcd. for C$_{22}$H$_{17}$N$_5$OS.¼H$_2$O C 65.41, H 4.37, N 17.34

Found: 65.41, H 4.18, N 17.18

What is claimed is:

1. A pyrazolopyridine compound of the following formula (I):

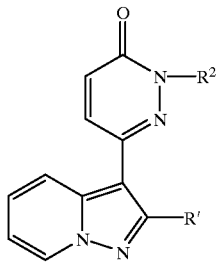 (I)

wherein
- $R^1$ is aryl, and
- $R^2$ is lower alkyl substituted with the thiazolyl group; lower alkyl substituted with unsaturated 3 to 8-membered heteromonocyclic group containing 1 or 2 sulfur atom(s) and 1 to 3 nitrogen atom(s) which has one or more substituent(s);

a group of the formula:

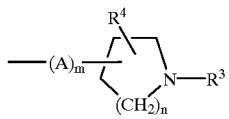

wherein
- $R^3$ is lower alkyl, ar(lower)alkyl or acyl,
- $R^4$ is hydrogen or hydroxy,
- A is lower alkylene,
- m is an integer of 0 or 1, and
- n is an integer of 1 to 2;

a group of the formula:

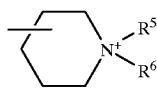

wherein
- $R^5$ and $R^6$ are each lower alkyl; or quinuclidinyl, or a salt thereof.

2. A compound of claim 1, wherein $R^1$ is phenyl, and $R^2$ is lower alkyl substituted with thiazolyl which may have 1 to 3 lower alkyl substituents;

a group of the formula:

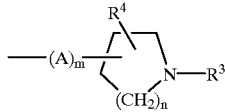

wherein
- $R^3$ is lower alkyl, phenyl(lower)alkyl, lower alkanoyl, lower alkoxycarbonyl, or phenyl(lower)alkoxycarbonyl,
- $R^4$ is hydrogen or hydroxy,
- A is lower alkylene,
- m is an integer of 0 or 1, and
- n is an integer of 1 or 2;

a group of the formula:

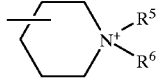

wherein
- $R^5$ and $R^6$ are each lower alkyl; or quinuclidinyl, or a salt thereof.

3. A compound of claim 2, wherein $R^2$ is lower alkyl substituted with thiazolyl which may have 1 to 3 lower alkyl substituents, or a salt thereof.

4. A compound of claim 2, wherein $R^2$ is a group of the formula:

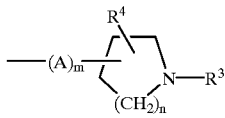

wherein
- $R^3$ is lower alkyl, phenyl(lower)alkyl, lower alkanoyl, lower alkoxycarbonyl, or phenyl(lower)alkoxycarbonyl,
- $R^4$ is hydrogen or hydroxy,
- A is lower alkylene,
- m is an integer of 0 or 1, and
- n is an integer of 1 or 2, or a salt thereof.

5. A compound of claim 4, wherein $R^2$ is a group of the formula:

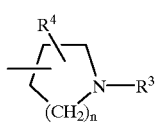

wherein
- $R^3$ is lower alkyl, phenyl(lower)alkyl, lower alkanoyl, or lower alkoxycarbonyl,
- $R^4$ is hydrogen, and
- n is an integer of 1 or 2, or a salt thereof.

6. A compound of claim 5, wherein $R^2$ is a group of the formula:

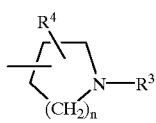

wherein
- $R^3$ is lower alkyl, phenyl(lower)alkyl, lower alkanoyl, or lower alkoxycarbonyl,
- $R^4$ is hydrogen, and
- n is an integer of 2, or a salt thereof.

7. A compound of claim 6, wherein $R^2$ is a group of the formula:

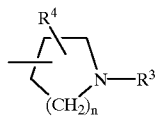

wherein $R^3$ is lower alkyl, $R^4$ is hydrogen, and n is an integer of 2, or a salt thereof.

8. A compound of claim 4, wherein $R^2$ is a group of the formula:

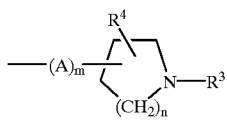

wherein $R^3$ is lower alkyl, lower alkanoyl, or phenyl(lower) alkoxycarbonyl, $R^4$ is hydrogen or hydroxy, A is lower alkylene, m is an integer of 1, and n is an integer of 1 or 2, or a salt thereof.

9. A compound of claim 8, wherein $R^2$ is a group of the formula:

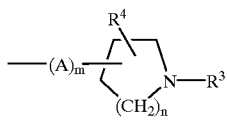

wherein $R^3$ is lower alkyl, $R^4$ is hydrogen,

A is lower alkylene, m is an integer of 1, and n is an integer of 1 or 2, or a salt thereof.

10. A process for the preparation of the pyrazolopyridine compound of claim 1 or a salt thereof, which comprises, (1) reacting a compound of the formula (II):

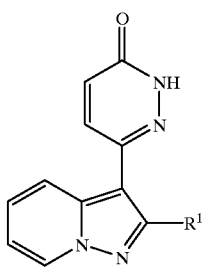

(II)

wherein $R^1$ is as defined in claim 8, or a salt thereof, with a compound of the formula (III);

X—$R^2$     (III)

wherein $R^2$ is as defined in claim 8 and X is a leaving group, to give a compound of the formula (I):

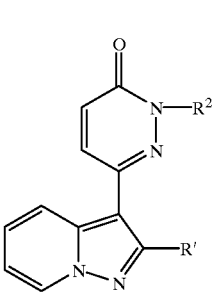

(I)

wherein $R^1$ and $R^2$ are each as defined in claim 8, or a salt thereof, (2) reacting a compound of the formula (II):

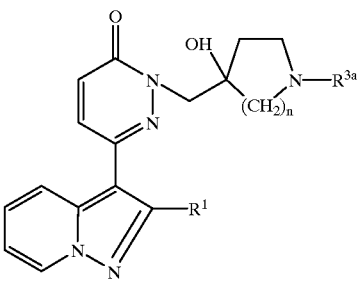

(Ia)

wherein $R^1$ is as defined in claim 8, or a salt thereof, with a compound of the formula (IV):

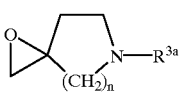

(IV)

wherein n is as defined in claim 8 and $R^{3a}$ is acyl, to give a compound of formula (Ia):

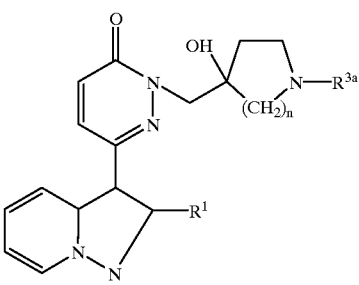

(Ia)

wherein $R^1$ and $R^3$ are each as defined above, or a salt thereof, (3) subjecting a compound of the formula (Ic):

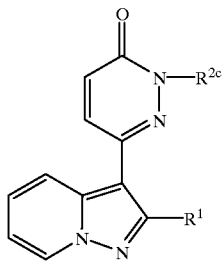

(Ic)

wherein $R^1$ is as defined above, and $R^{2c}$ is a group of the formula:

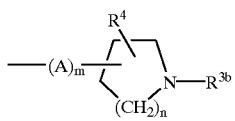

wherein A, m, n and $R^4$ are each as defined above, $R^{3b}$ is hydrogen, or a salt thereof, to alkylation reaction, to give a compound of the formula (Ie):

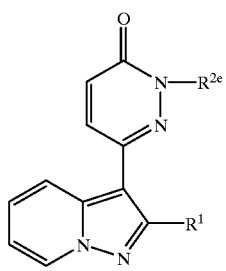

(Ie)

wherein $R^1$ is as defined in claim 8 and $R^{2e}$ is a group of the formula:

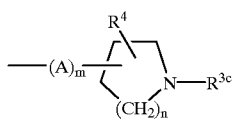

wherein A, m, n, and $R^4$ are each as defined above, and $R^{3c}$ is lower alkyl, or a group of the formula:

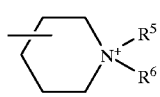

wherein $R^5$ and $R^6$ are each as defined in claim 8, or a salt thereof, (4) subjecting a compound of the formula (Ic):

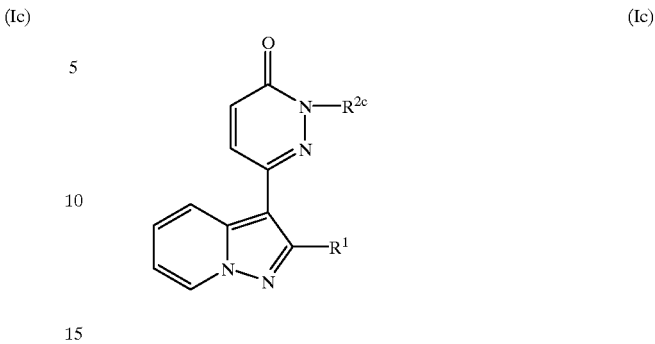

(Ic)

wherein $R^1$ and $R^{2c}$ are each as defined above, or a salt thereof, to acylation reaction, to give a compound of the formula (Ib):

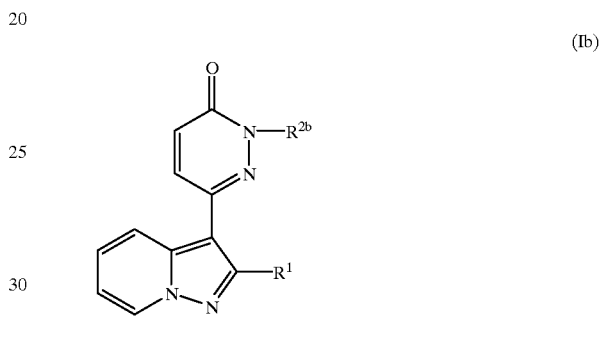

(Ib)

wherein $R^1$ is as defined above and $R^{2b}$ is a group of the formula:

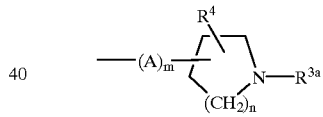

wherein A, m, n, $R^4$ and $R^{3a}$ are each as define above, or a salt thereof, or (5) subjecting the compound of formula (V):

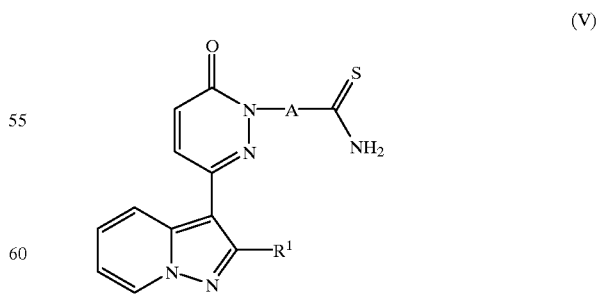

(V)

wherein $R^1$ and A are each as defined in claim 8, or a salt thereof, to formation reaction of thiazole ring, to give a compound of the formula (If):

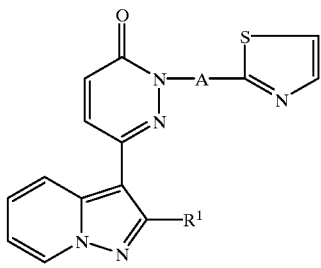

(If)

wherein R¹ and A are each as defined above, or a salt thereof.

11. A pharmaceutical composition comprising the compound of claim 1 or a salt thereof in association with a pharmaceutically acceptable carrier or excipient.

12. A method for treating a diseases selected from the group consisting of depression, dementia, anxiety, pain, cerebrovascular disease, heart failure, hypertension, circulatory insufficiency, post-resuscitation, asystole, bradyarrhythmia, electro-mechanical dissociation, hemodynamic collapse, SIRS (systemic inflammatory response syndrome), multiple organ failure, renal failure (renal insufficiency), renal toxicity, nephrosis, nephritis, edema, obesity, bronchial asthma, gout, hyperuricemia, sudden infant death syndrome, immunosuppression, diabetes, ulcer, pancreatitis, Menier's syndrome, anemia, dialysis-induced hypotention, constipation, ischemic bowel disease, ileus, myocardial infarction, thrombosis obstruction, arteriosclerosis obliterans, thrombophlebitis, cerebral infarction, transient ischemic attack and angina pectoris, which comprises administering the compound of claim 1 or a salt thereof to a human being or an animal.

13. A process for preparing a pharmaceutical composition which comprises admixing the compound of claim 1 or a salt thereof with pharmaceutically acceptable carriers or excipients.

14. A pharmaceutical composition comprising the compound of claim 1 or a salt thereof in an adenosine antagonist effective amount in association with a pharmaceutically acceptable carrier or excipient.

* * * * *